(12) United States Patent
Takada et al.

(10) Patent No.: US 10,930,854 B2
(45) Date of Patent: Feb. 23, 2021

(54) MONOAMINE MATERIAL FOR ORGANIC ELECTROLUMINESCENT ELEMENT, AND ORGANIC ELECTROLUMINESCENT ELEMENT USING SAME

(71) Applicant: SAMSUNG DISPLAY CO., LTD., Yongin-si (KR)

(72) Inventors: Ichinori Takada, Yokohama (JP); Naoya Sakamoto, Yokohama (JP)

(73) Assignee: Samsung Display Co., Ltd., Yongin-si (KR)

(*) Notice: Subject to any disclaimer, the term of this patent is extended or adjusted under 35 U.S.C. 154(b) by 0 days.

(21) Appl. No.: 15/322,292

(22) PCT Filed: Aug. 11, 2015

(86) PCT No.: PCT/KR2015/008398
§ 371 (c)(1),
(2) Date: Dec. 27, 2016

(87) PCT Pub. No.: WO2016/024792
PCT Pub. Date: Feb. 18, 2016

(65) Prior Publication Data
US 2017/0133591 A1    May 11, 2017

(30) Foreign Application Priority Data

Aug. 11, 2014 (JP) .............................. JP2014-163347
Aug. 7, 2015 (JP) .............................. JP2015-156701

(51) Int. Cl.
*H01L 51/50* (2006.01)
*H01L 51/00* (2006.01)
(Continued)

(52) U.S. Cl.
CPC .......... *H01L 51/006* (2013.01); *C07D 307/91* (2013.01); *C07D 333/76* (2013.01);
(Continued)

(58) Field of Classification Search
None
See application file for complete search history.

(56) References Cited

U.S. PATENT DOCUMENTS

| 4,720,432 A | 1/1988 | Vanslyke et al. |
| 8,652,654 B2 | 2/2014 | Inoue et al. |

(Continued)

FOREIGN PATENT DOCUMENTS

| CN | 101805266 A | 8/2010 |
| CN | 102203213 A | 9/2011 |

(Continued)

OTHER PUBLICATIONS

Office Action issued in U.S. Appl. No. 14/832,292 by the USPTO, dated Apr. 12, 2017.

(Continued)

*Primary Examiner* — Gregory D Clark
(74) *Attorney, Agent, or Firm* — Lewis Roca Rothgerber Christie LLP

(57) ABSTRACT

Provided are a material for an organic electroluminescence device and an organic electroluminescence device including the same. The material for an organic electroluminescence device is a monoamine compound represented by the following General Formula (1).

(Continued)

[Formula 1]

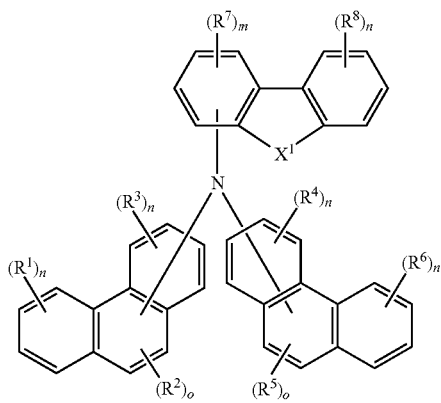

(1)

where $X^1$ is one selected from O, S, $R^9$—C—$R^{10}$, or N—$R^{11}$, $R^1$ to $R^{11}$ are each independently alkyl having 10 or less carbon atoms, aryl having 6 to 30 carbon atoms for forming a ring, alkyloxy, alkylthio, trialkylsilyl, aryloxy, arylthio, triarylsilyl, alkyldiarylsilyl, dialkylarylsilyl, or heteroaryl having 2 to 30 carbon atoms for forming a ring, n is an integer of 0 to 4, m is an integer of 0 to 3, and o is an integer of 0 to 2.

9 Claims, 2 Drawing Sheets

(51) Int. Cl.
  *C07D 307/91* (2006.01)
  *C07D 333/76* (2006.01)
  *C09K 11/06* (2006.01)
(52) U.S. Cl.
  CPC .......... *C09K 11/06* (2013.01); *H01L 51/0061*
    (2013.01); *H01L 51/50* (2013.01); ***H01L
    51/0052* (2013.01); *H01L 51/0073*** (2013.01);
    *H01L 51/5056* (2013.01)

(56) References Cited

U.S. PATENT DOCUMENTS

| | | | |
|---|---|---|---|
| 2009/0091244 | A1 | 4/2009 | Negishi et al. |
| 2010/0108997 | A1 | 5/2010 | Kim et al. |
| 2011/0278551 | A1 | 11/2011 | Yabunouchi et al. |
| 2012/0203010 | A1 | 8/2012 | Matsumoto et al. |
| 2015/0155491 | A1* | 6/2015 | Mujica-Fernaud .......... C07D 219/02 252/500 |
| 2016/0118591 | A1 | 4/2016 | Yokoyama et al. |
| 2017/0018710 | A1 | 1/2017 | Mujica-Fernaud et al. |

FOREIGN PATENT DOCUMENTS

| | | | |
|---|---|---|---|
| CN | 102850334 A | 1/2013 | |
| EP | 1 584 614 A1 | 10/2005 | |
| EP | 2175005 A1 | 4/2010 | |
| EP | 2 343 277 A2 | 7/2011 | |
| JP | 2000-178666 A | 6/2000 | |
| JP | 2004-231547 A | 8/2004 | |
| JP | 2004345960 A | 12/2004 | |
| JP | 2010-132638 | 6/2010 | |
| JP | 4770033 B2 | 7/2011 | |
| JP | 2011-187959 A | 9/2011 | |
| JP | 5016018 B2 | 9/2012 | |
| JP | 2013-177386 A | 9/2013 | |
| JP | 2013-234169 A | 11/2013 | |
| KR | 10-0820830 B1 | 4/2008 | |
| KR | 2010007639 | * 1/2010 | ............ C09K 11/06 |
| KR | 10-2010-0041043 A | 4/2010 | |
| KR | 10-2010-0048210 A | 5/2010 | |
| KR | 10-0974562 B1 | 8/2010 | |
| KR | 10-2013-0007159 A | 1/2013 | |
| KR | 10-2013-0022232 A | 3/2013 | |
| KR | 10-1389527 B1 | 4/2014 | |
| WO | WO 0230159 A1 | 4/2002 | |
| WO | WO 2007/105906 A1 | 9/2007 | |
| WO | WO 2010/050779 A1 | 5/2010 | |
| WO | WO 2010/106806 A1 | 9/2010 | |
| WO | WO 2013/182263 A1 | 12/2013 | |
| WO | WO 2015/131976 A1 | 9/2015 | |

OTHER PUBLICATIONS

Office Action issued in U.S. Appl. No. 14/798,786 by the USPTO, dated Jun. 2, 2017, 20 pages.
Final Office Action issued in U.S. Appl. No. 14/798,786 by the USPTO, dated Nov. 27, 2017, 23 pages.

* cited by examiner

MONOAMINE MATERIAL FOR ORGANIC ELECTROLUMINESCENT ELEMENT, AND ORGANIC ELECTROLUMINESCENT ELEMENT USING SAME

CROSS REFERENCE TO RELATED APPLICATIONS

This application the U.S. national phase application based on PCT Application No. PCT/KR2015/008398, filed Aug. 11, 2015, which is based on Japanese Patent Application Nos. 2014-163347, filed Aug. 11, 2014, and 2015-156701, filed Aug. 7, 2015, the entire contents of all of which are hereby incorporated by reference.

This application claims priority under 35 U.S.C. § 120 to pending application Ser. No. 14/706,137, filed May 7, 2015, the entire contents of which is hereby incorporated by reference.

BACKGROUND

1. Field

The present disclosure herein relates to a material for an organic electroluminescence device and an electroluminescence device including the same. Particularly, the present disclosure relates to a hole transport material for an organic electroluminescence device having high efficiency and long life, and an electroluminescence device using the same.

2. Prior Art

Recently, as an image display apparatus, developments on an organic electroluminescence (EL) display are being actively conducted.

The organic EL display is different from a liquid crystal display and is a self-luminescent display attaining display by emitting a luminescent material including an organic compound in an emission layer via the recombination of holes and electrons respectively injected from an anode and a cathode in an emission layer.

As an organic EL device, an organic device including, for example, an anode, a hole transport layer disposed on the anode, an emission layer disposed on the hole transport layer, an electron transport layer disposed on the emission layer, and a cathode disposed on the electron transport layer is known. Holes are injected from the anode, and the injected holes move via the hole transport layer and are injected to the emission layer. Meanwhile, electrons are injected from the cathode, and the injected electrons move via the electron transport layer and are injected to the emission layer. The holes and the electrons injected to the emission layer recombine to produce excitons in the emission layer. The organic EL device may emit light via the radiation deactivation of the excitons. In addition, the configuration of the organic EL device is not limited to the above-described configuration, however various modifications may be possible.

For the application of the organic EL device to a display, the increase of the emission efficiency and life of the organic EL device is required. To attain the high emission efficiency and long life of the organic EL device, the normalization, the stabilization, the increase of durability, etc. of a hole transport layer, etc. are examined.

As a hole transport material used in the hole transport layer, various compounds such as an aromatic amine compound is known. For example, amine compounds disclosed in Patent Documents 1-3 are suggested.

However, since an aromatic amine compound has low electron tolerance, it is difficult to say that an organic EL device using the material has sufficient emission life.

In addition, since a common hole transport material is lack of inhibiting properties on the transport of electrons which are not consumed in an emission layer and reached a layer near an anode, the deterioration of the material of the layer near the anode due to the electrons became one factor of decreasing emission efficiency and life of an organic EL device.

Accordingly, an organic EL device having further higher efficiency and long emission life is preferable as of now. Particularly, since the emission efficiency of an organic EL device in a blue emission region is lower than in a red emission region and a green emission region, the improvement of emission efficiency is required.

PRIOR ART DOCUMENTS

Patent Documents (Patent Document 1) JPH02-178666 A
(Patent Document 2) JP4090874 B
(Patent Document 3) KR10-820830 B

SUMMARY

The present disclosure provides a material for an organic EL device having long life and an organic EL device using the same to solve the above-described defects.

An embodiment of the present disclosure provides a monoamine material for an organic EL device, represented by the following General Formula (1).

[Formula 1]

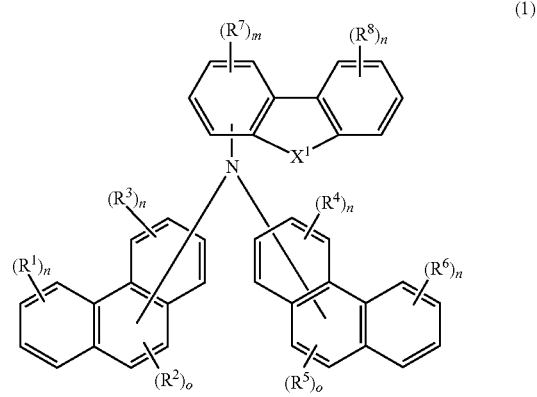

In General Formula (1), $X^1$ is one selected from O, S, $R^9$—C—$R^{10}$, or N—$R^{11}$, $R^1$ to $R^{11}$ are each independently alkyl having 10 or less carbon atoms, aryl having 6 to 30 carbon atoms for forming a ring, alkyloxy, alkylthio, trialkylsilyl, aryloxy, arylthio, triarylsilyl, alkyldiarylsilyl, dialkylarylsilyl, or heteroaryl having 2 to 30 carbon atoms for forming a ring, n is an integer of 0 to 4, m is an integer of 0 to 3, and o is an integer of 0 to 2.

By introducing two phenanthrene parts to an amine in the monoamine material for an organic EL device according to an embodiment of the present disclosure, hole transport property and electron tolerance may be improved, and the inhibition of electron transfer may become possible, thereby forming a hole transport layer having high efficiency and long life in an organic EL device.

In an embodiment, a phenanthryl group in General Formula (1) may be combined with a nitrogen atom at a position other than position 9 or position 10.

By introducing two phenanthrene parts to an amine in the monoamine material for an organic EL device according to an embodiment of the present disclosure, hole transport property and electron tolerance may be improved, and the inhibition of electron transfer may become possible, thereby forming a hole transport layer having high efficiency and long life in an organic EL device.

In an embodiment of the present disclosure, a monoamine material for an organic EL device, represented by the following General Formula (2) is provided.

[Formula 2]

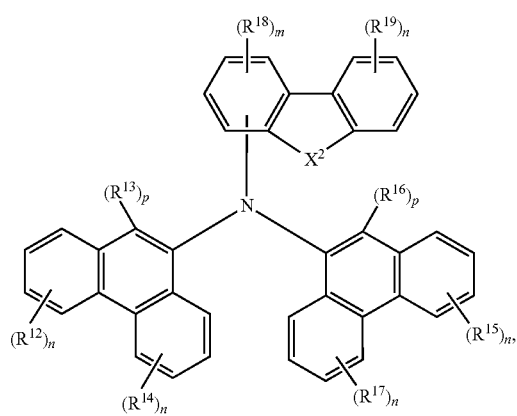

(2)

In General Formula (2), $X^2$ is O or S. $R^{12}$ to $R^{19}$ are each independently alkyl having 10 or less carbon atoms, aryl having 6 to 30 carbon atoms for forming a ring, alkyloxy, alkylthio, trialkylsilyl, aryloxy, arylthio, triarylsilyl, alkyldiarylsilyl, dialkylarylsilyl, or heteroaryl having 2 to 30 carbon atoms for forming a ring, n is an integer of 0 to 4, m is an integer of 0 to 3, and p is an integer of 0 or 1.

By introducing two phenanthrene parts to an amine in the monoamine material for an organic EL device according to an embodiment of the present disclosure, hole transport property and electron tolerance may be improved, and the inhibition of electron transfer may become possible, thereby forming a hole transport layer having high efficiency and long life in an organic EL device.

In an embodiment of the present disclosure, an organic EL device including the material for an organic EL device in at least one layer laminated between an emission layer and an anode is provided.

By including a monoamine material for an organic EL device, in which two phenanthrene parts are introduced to an amine in at least one layer laminated between an emission layer and an anode, hole transport property and electron tolerance may be improved, and the inhibition of electron transfer may become possible for the organic EL device according to an embodiment of the present disclosure, thereby attaining high efficiency and long life.

In an embodiment of the present disclosure, an organic EL device including the material for an organic EL device in a layer laminated between an emission layer and an anode, wherein the layer is adjacent to the emission layer, is provided.

By including a monoamine material for an organic EL device, in which two phenanthrene parts are introduced to an amine in at least one layer laminated between an emission layer and an anode, wherein the layer is adjacent to the emission layer, the effective inhibition of electron transfer to a layer adjacent to the anode may become possible for the organic EL device according to an embodiment of the present disclosure, thereby attaining high efficiency and long life.

BRIEF DESCRIPTION OF THE FIGURES

The accompanying drawings are included to provide a further understanding of the present disclosure, and are incorporated in and constitute a part of this specification. The drawings illustrate exemplary embodiments of the present disclosure and, together with the description, serve to explain principles of the present disclosure. In the drawings.

DETAILED DESCRIPTION

Figure 1:
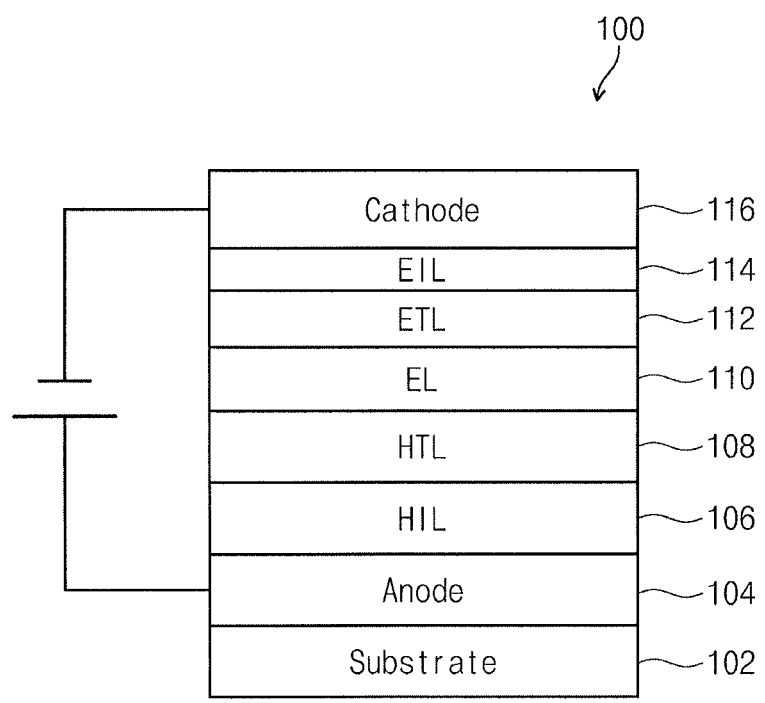
FIG. 1 is a schematic view illustrating an organic EL device 100 according to an embodiment of the present disclosure.
Figure 2:
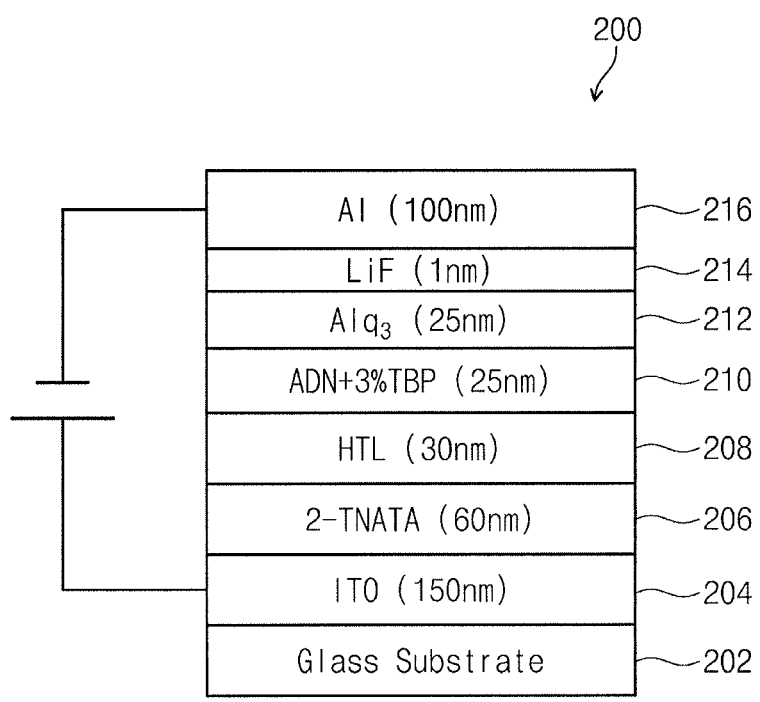
FIG. 2 is a schematic view illustrating an organic EL device 200 according to an embodiment of the present disclosure.

After thorough examination to solve the above limitations, the present inventors found that an organic EL device having high efficiency and long life may be attained by using a monoamine material for an organic EL device, which introduces two phenanthrene parts to a monoamine, and completed the present disclosure. Hereinafter, a monoamine material for an organic EL device and an organic EL device using the same will be explained.

The monoamine material for an organic EL device and the organic EL device using the same according to the present disclosure may, however, be embodied in different forms and should not be construed as limited to the embodiments set forth herein. In the drawings referenced by embodiments, the same reference numerals are designated for explaining the same part or parts having the same function and repeated explanation thereon will be omitted.

A material for an organic EL device according to the present disclosure is a monoamine compound in which two phenanthryl groups are combined with the nitrogen atom (N) of an amine, represented by the following General Formula (1).

[Formula 1]

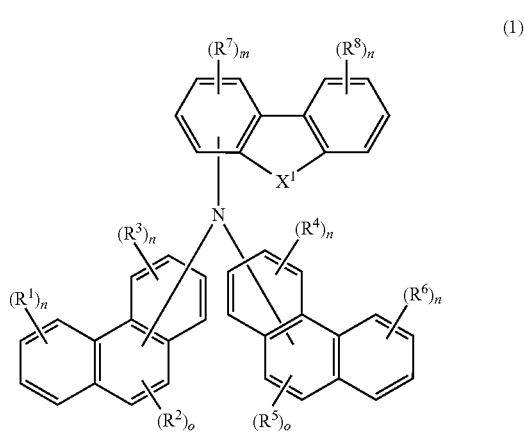

(1)

In General Formula (1) as the monoamine material for an organic EL device according to the present disclosure, $X^1$ is one selected from O, S, $R^9$—C—$R^{10}$, or N—$R^{11}$, $R^1$- to $R^{11}$ are each independently alkyl having 10 or less carbon atoms, aryl having 6 to 30 carbon atoms for forming a ring, alkyloxy, alkylthio, trialkylsilyl, aryloxy, arylthio, triarylsilyl, alkyldiarylsilyl, dialkylarylsilyl, or heteroaryl having 2 to 30 carbon atoms for forming a ring, n is an integer of 0 to 4, m is an integer of 0 to 3, and o is an integer of 0 to 2.

$R^1$ to $R^{11}$ may particularly include methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropy, 2,3-diiodo-t-butyl, 1,2,3-triiodopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, 1,2,3-trinitropropyl, cyclopropyl, cyclobutyl, cyclopentyl, cyclohexyl, 4-methylcyclohexyl, 1-adamantyl, 2-adamantyl, 1-adamantyl, 2-adamantyl, 1-norbornyl, 2-norbornyl, 1-norbornyl, 2-norbornyl, phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4"-t-butyl-p-terphenyl-4-yl, fluoranthenyl, fluorenyl, 1-pyrrolyl, 2-pyrrolyl, 3-pyrrolyl, pyridinyl, 2-pyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofurany, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalyl, 5-quinoxalyl, 6-quinoxalyl, 1-carbazolyl, 2-carbazolyl, 3-carbazolyl, 4-carbazolyl, 9-carbazolyl, 1-dibenzofuranyl, 2-dibenzofuranyl, 3-dibenzofuranyl, 4-dibenzofuranyl, 1-dibenzothiazolyl, 2-dibenzothiazolyl, 3-dibenzothiazolyl, 4-dibenzothiazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-t-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-t-butyl1-indolyl, 4-t-butyl1-indolyl, 2-t-butyl3-indolyl, 4-t-butyl3-indolyl, etc., without limitation.

In the monoamine material for an organic EL device according to the present disclosure, a plurality of adjacent $R^1$ to $R^{11}$ in General Formula (1) may combine to form a saturated or unsaturated 5 to 7 member ring.

The monoamine material for an organic EL device according to the present disclosure may be General Formula (1) wherein two phenanthryl groups are combined with the nitrogen atom (N) of an amine at position 9 or position 10, respectively.

That is, in the case where two phenanthryl groups are combined with the nitrogen atom (N) of an amine at position 9 or position 10 in General Formula (1), the monoamine material for an organic EL device according to the present disclosure may be represented by the following General Formula (2).

[Formula 2]

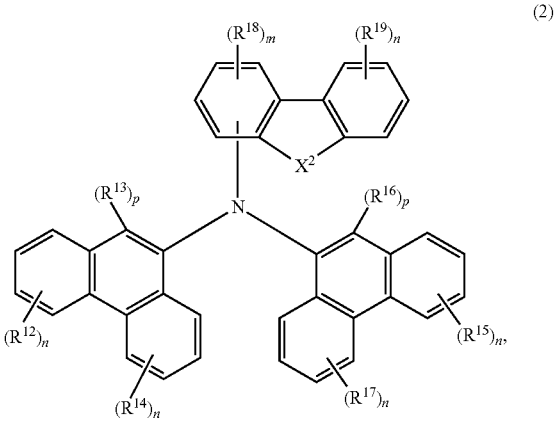

(2)

In General Formula (2), $X^2$ is O or S, $R^{12}$ to $R^{19}$ are each independently alkyl having 10 or less carbon atoms, aryl having 6 to 30 carbon atoms for forming a ring, alkyloxy, alkylthio, trialkylsilyl, aryloxy, arylthio, triarylsilyl, alkyldiarylsilyl, dialkylarylsilyl, or heteroaryl having 2 to 30 carbon atoms for forming a ring, n is an integer of 0 to 4, m is an integer of 0 to 3, and p is an integer of 0 or 1.

As $R^{12}$ to $R^{19}$, the same functional groups as for $R^1$-$R^{11}$ in General Formula (1) may be used.

In addition, in General Formula (1), a plurality of adjacent $R^{12}$ to $R^{19}$ may combine to form a saturated or unsaturated 5- to 7 member ring.

In addition, in the monoamine material for an organic EL device according to the present disclosure, two phenanthryl groups may be combined with the nitrogen atom (N) of an amine at a position other than position 9 or position 10, respectively. Alternatively, in General Formula (1), one of the two phenanthryl groups may be combined with the nitrogen atom (N) of an amine at position 9 or position 10, and the other group may be combined with the nitrogen atom (N) at a position other than position 9 or position 10. That is, two phenanthryl groups may be asymmetrically combined with the nitrogen atom (N) of an amine.

The material for an organic EL device according to the present disclosure may be, for example, materials represented by the following structures.

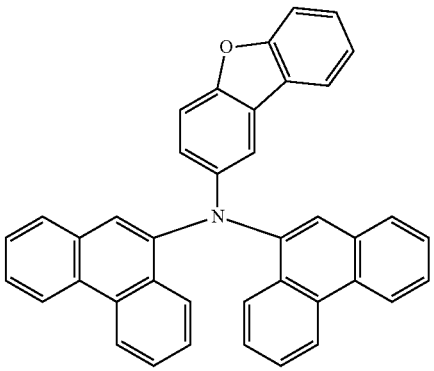

1

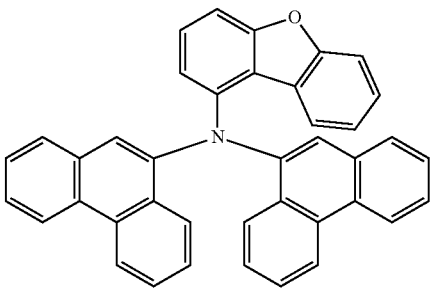

2

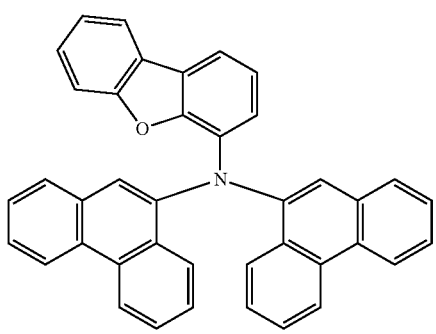

3

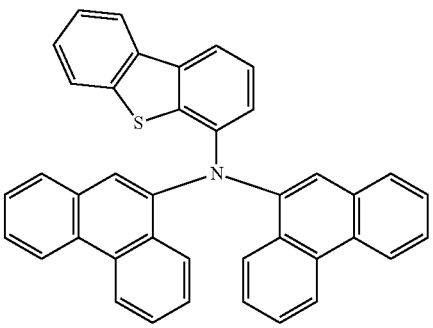

4

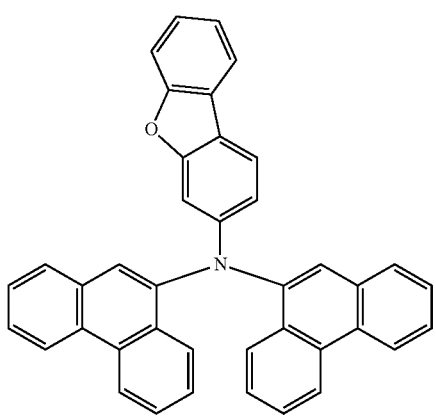

5

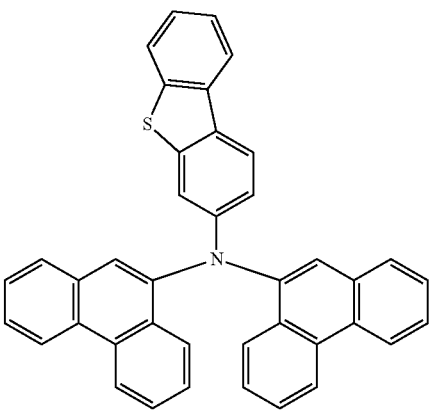

6

7
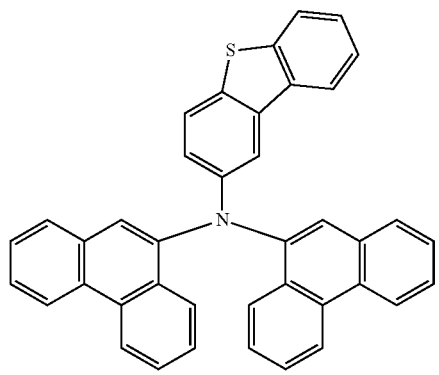
8
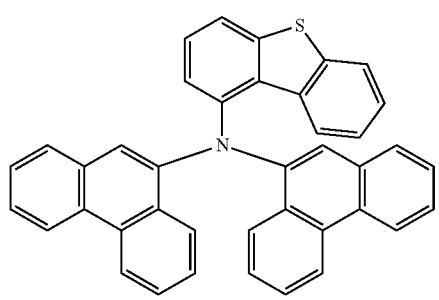
9
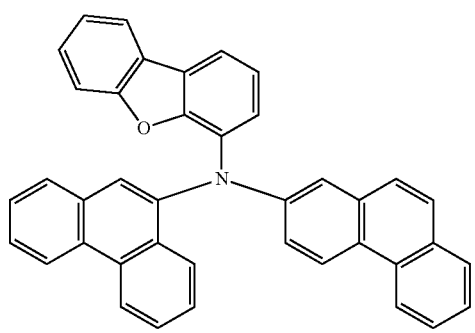
10
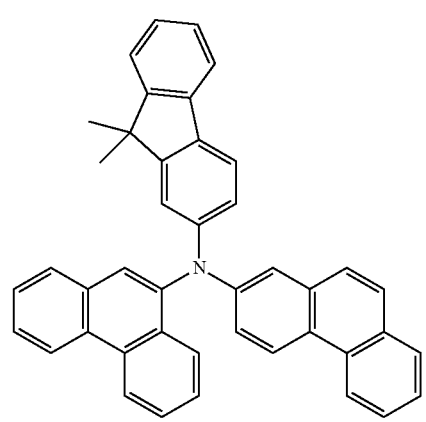
11
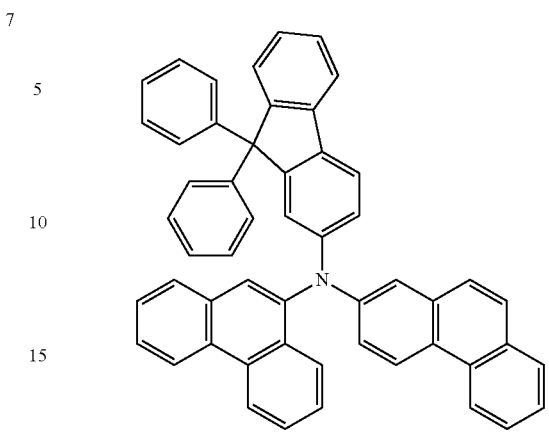
12
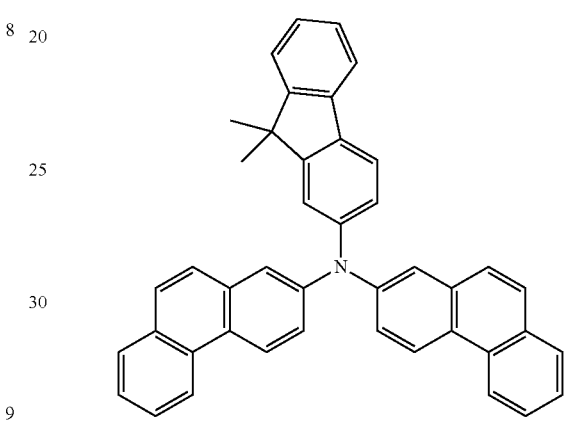
13
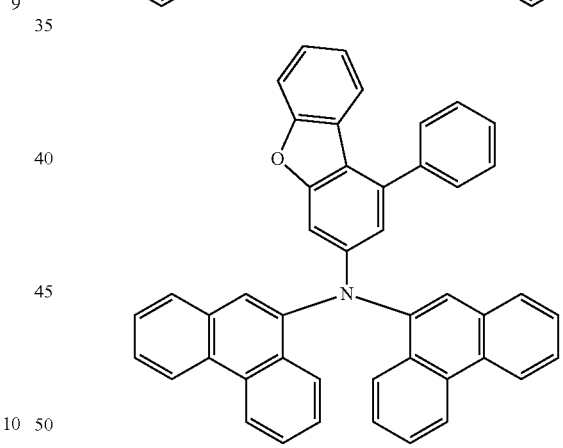
14
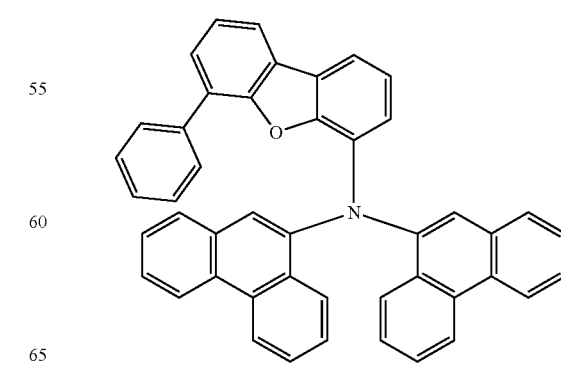

15
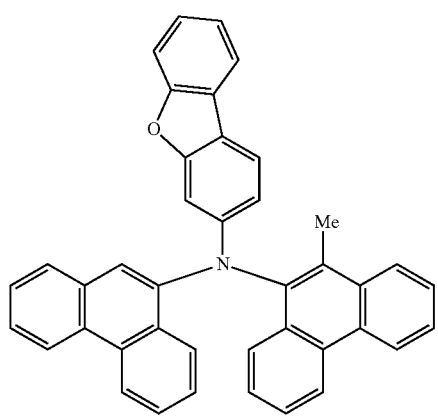
16
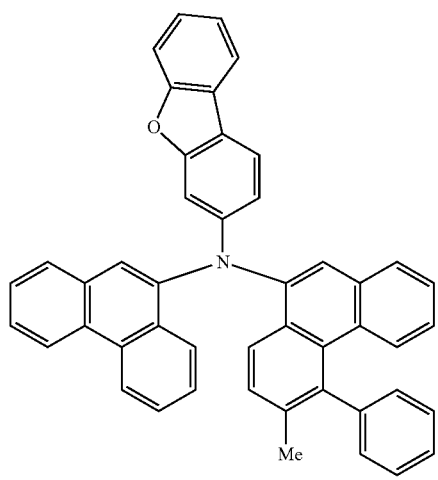
17
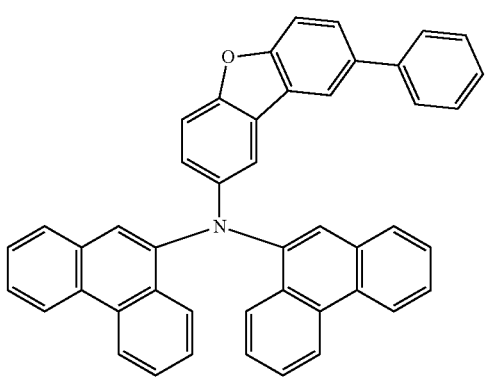
18
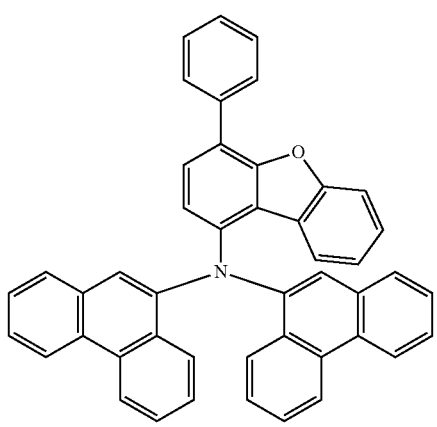
19
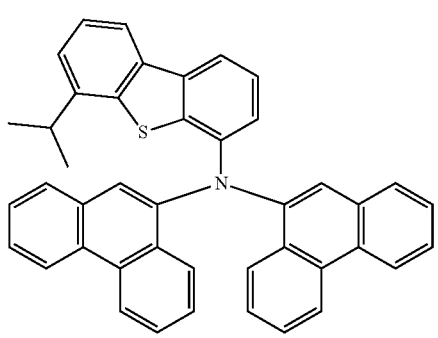
20
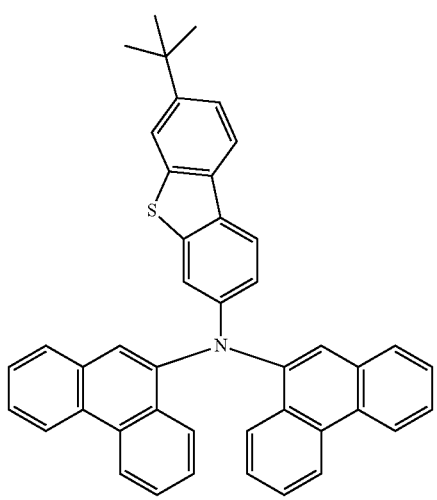
21
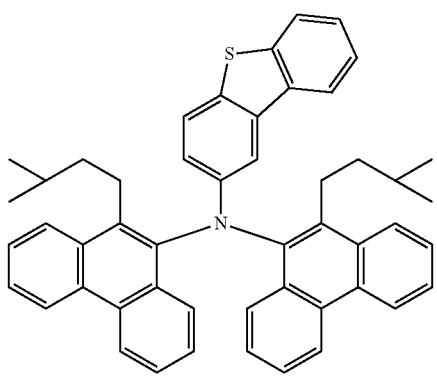

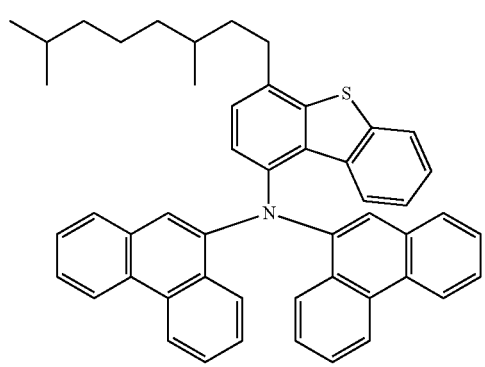
22
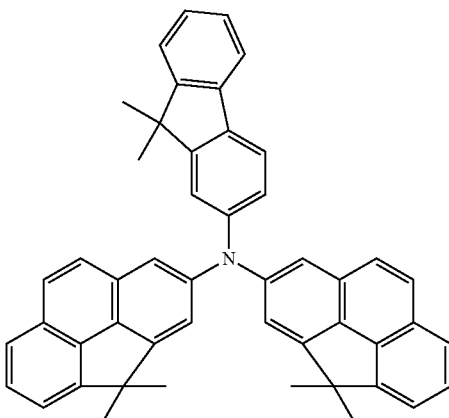
26
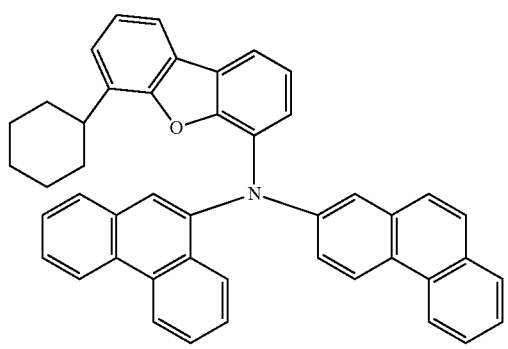
23
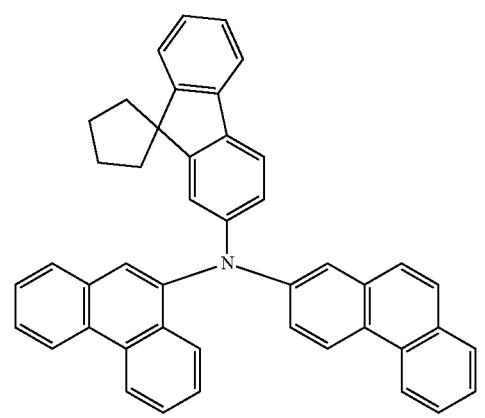
24
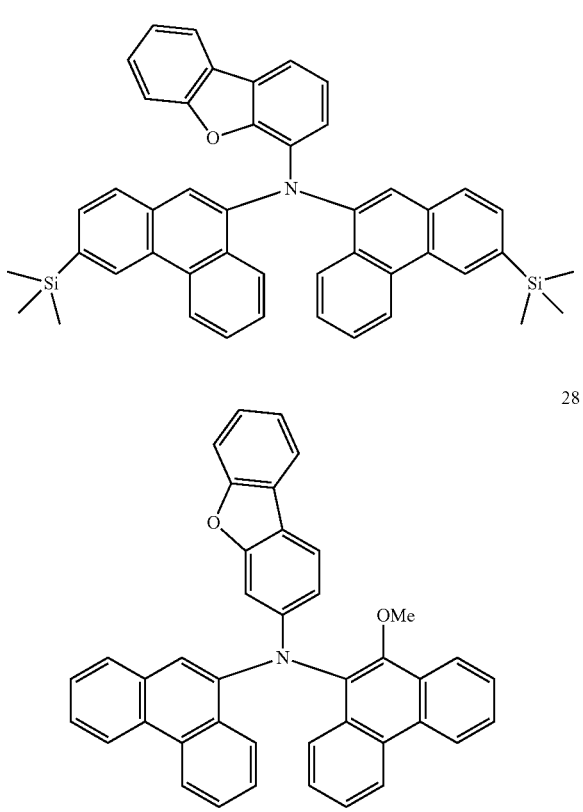
27
28
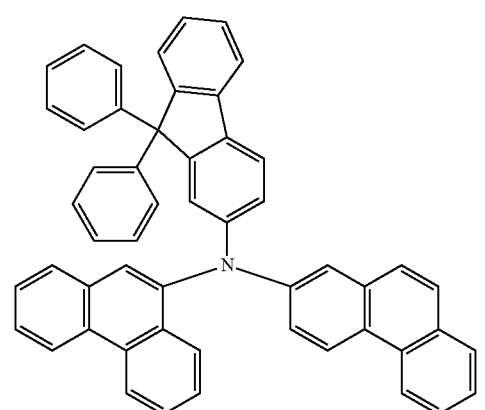
25
29

30

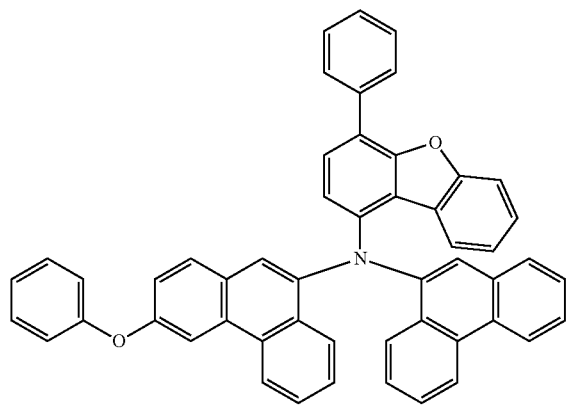

31

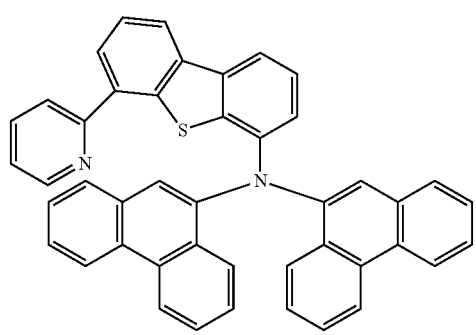

32

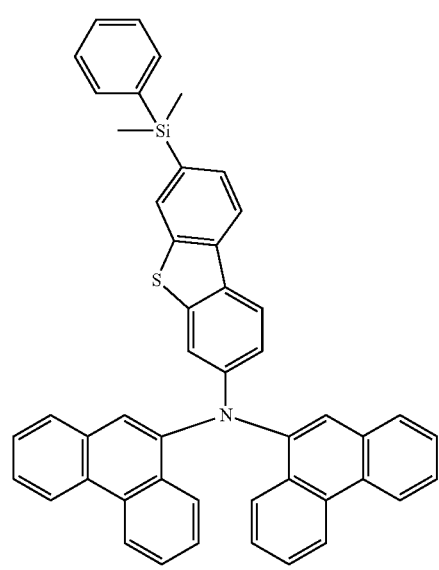

33

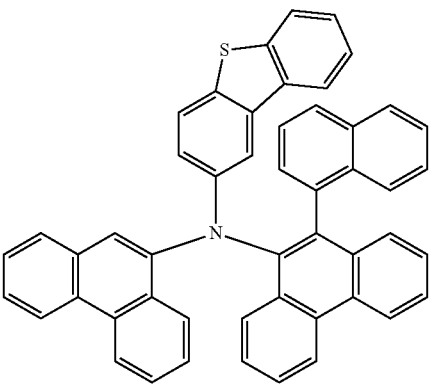

34

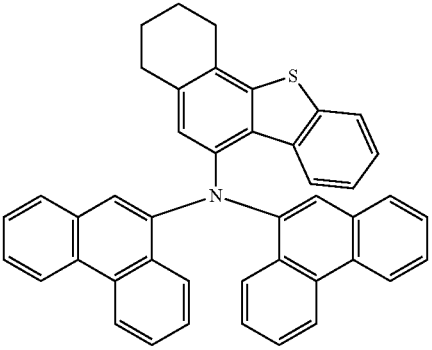

The monoamine material for an organic EL device according to the present disclosure introduces two phenanthryl parts to a monoamine, and the hole transport properties and electron tolerance thereof may be improved. Accordingly, by using the monoamine material for an organic EL device according to the present disclosure as a material for a layer present between an anode and an emission layer, an organic EL device having high efficiency and long life may be attained.

In addition, in the monoamine material for an organic EL device according to the present disclosure, two phenanthryl groups are introduced to a monoamine, thereby inhibiting the transfer of electrons.

The transfer of electrons which are not consumed in an emission layer but reached a layer disposed near an anode, may be inhibited, and accordingly, the monoamine material for an organic EL device according to the present disclosure is used as a material of a layer present between an anode and an emission layer, so as to restrain the deterioration due to electrons in the layer disposed near the anode and attain the increase of life of an organic EL device.

The monoamine material for an organic EL device according to the present disclosure may be used as a material of at least one layer present between an anode and an emission layer in an organic EL device.

In particular, the monoamine material for an organic EL device according to the present disclosure may preferably be used as a material of a hole transport layer.

In the case where a hole transport layer has a multilayer structure, the material may preferably be used as a material of a layer disposed near an emission layer, and may particularly preferably be used as a material of a layer adjacent to the emission layer in the multilayer structure.

By using the monoamine material for an organic EL device according to the present disclosure as a material of a layer near or adjacent to an emission layer among layers present between an anode and an emission layer, the diffusion of electrons not consumed in the emission layer, to a layer disposed near the anode may be effectively restrained. Therefore, the deterioration of a layer disposed near the anode due to electrons may decrease, and the increase of life of an organic EL device may be attained.

(Organic EL Device)

An organic EL device using the monoamine material for an organic EL device according to the present disclosure will be explained. FIG. 1 is a schematic diagram of an organic EL device 100 according to an embodiment of the present disclosure.

An organic EL device 100 includes, for example, a substrate 102, an anode 104, a hole injection layer 106, a hole transport layer 108, an emission layer 110, an electron transport layer 112, an electron injection layer 114, and a cathode 116.

In an embodiment, the monoamine material for an organic EL device according to the present disclosure may be used in at least one layer of laminated layers disposed between an emission layer and an anode. In an embodiment, a case where the monoamine material for an organic EL device according to the present disclosure is used in the hole transport layer 108 will be explained, as an example.

The substrate 102 may be, for example, a transparent glass substrate, a semiconductor substrate formed using silicon, etc., or a flexible substrate of a resin, etc. The anode (Anode) 104 is disposed on the substrate 102 and may be formed using indium tin oxide (ITO), indium zinc oxide (IZO), etc. The hole injection layer (HIL) 106 is disposed on the anode 104 and may include, for example, 4,4',4"-tris(N-1-naphthyl-N-phenylamino)triphenylamine (1-TNATA), 4,4',4"-tris(N-(2-naphthyl)-N-phenylamino)-triphenylamine (2-TNATA), 4,4-bis(N,N-di(3-tolyl)amino)-3,3-dimethylbiphenyl (HMTPD), etc. The hole transport layer (HTL) 108 is disposed on the hole injection layer and is formed using the monoamine material for an organic EL device according to the present disclosure. The emission layer (EL) 110 is disposed on the hole transport layer 108 and may be formed by, for example, doping 9,10-di(2-naphthyl)anthracene (ADN) with tetra-t-butylperylene (TBP).

The electron transport layer (ETL) 112 is disposed on the emission layer 110 and is formed using, for example, a material including tris(8-hydroxyquinolinato)aluminum (Alq$_3$). The electron injection layer (EIL) 114 is disposed on the electron transport layer 112 and is formed by, for example, a material including lithium fluoride (LiF).

The cathode (Cathode) 116 is disposed on the electron injection layer 114 and is formed by a metal such as Al or a transparent material such as ITO and IZO. The thin film may be formed by selecting an appropriate layer forming method such as a vacuum deposition method, a sputtering method, and various coating methods depending on the material used.

In the organic EL device 100 according to the present disclosure, by using the monoamine material for an organic EL device according to the present disclosure, the deterioration of a layer present near an anode due to electrons may be restrained, and the increase of efficiency and life of the organic EL device 100 may be attained. In addition, in the organic EL device 100, the monoamine material for an organic EL device according to the present disclosure may be used as a material of a hole injection layer.

As described above, by using the monoamine material for an organic EL device according to the present disclosure in at least one layer laminated between an emission layer and an anode, the increase of efficiency and life of an organic EL device may be attained. In addition, the monoamine material for an organic EL device according to the present disclosure may be applied to an organic EL light-emitting display of an active matrix type using a TFT. In addition, even a TBP fluorescent material is used as a dopant material in an emission layer in the organic EL device 100, a phosphorescent compound may be also used as a material of an emission layer in the organic EL device according to the present disclosure.

(Preparation Method)

A monoamine material for an organic EL device according to the present disclosure may be synthesized by reacting the following Compound 35 or an arylamine compound having a similar structure with a halogen compound of an aryl compound such as phenanthrene or a heteroaryl compound using a Pd catalyst, etc. The monoamine material for an organic EL device according to the present disclosure may be synthesized, for example, as follows.

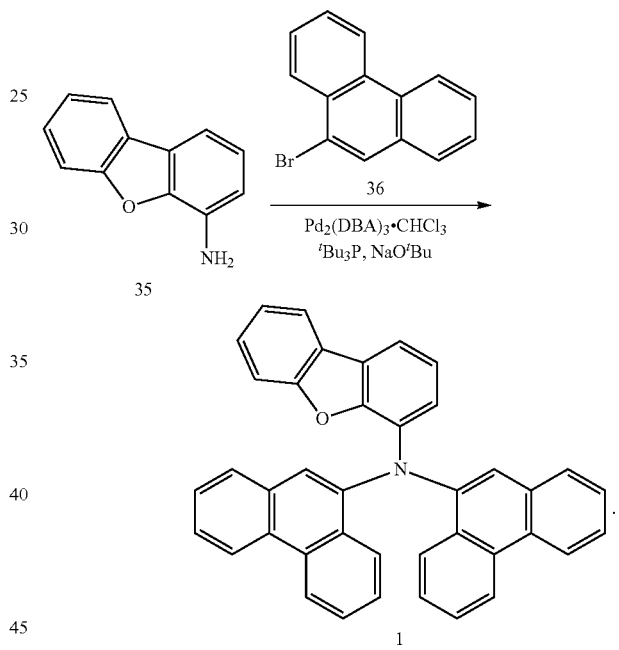

(Synthesis of Compound 1)

A mixture of Compound 35 (dibenzofuranamine, 2.20 g, 12.0 mmol), Compound 36 (bromophenanthrene, 6.31 g, 24.5 mmol), sodium-tert-butoxide (NaO$^t$Bu, 3.45 g, 35.9 mmol), tris(dibenzylideneacetone)dipalladium(0)chloroform adduct (Pd$_2$(DBA)$_3$.CHCl$_3$, 620 mg, 0.599 mmol), and anhydrous xylene (150 mL) was degassed, and an 1.6M-tri-tert-butylphosphine ($^t$Bu$_3$P) solution (749 L, 1.20 mmol) was added thereto.

The mixture was heated and refluxed for about 12 hours, cooled, and filtered. The filtrate was concentrated and separated by directly using column chromatography to obtain Compound 1 (3.53 g, 55%) as a white powder.

(Identification Method of Compound 1)

The identification of Compound 1 was conducted by detecting molecular ion peak in FAB-MS measurement. The molecular weight of Compound 1 measured by FAB-MS was 535. In addition, the monoamine material for an organic EL device according to the present disclosure may be synthesized, for example, as follows.

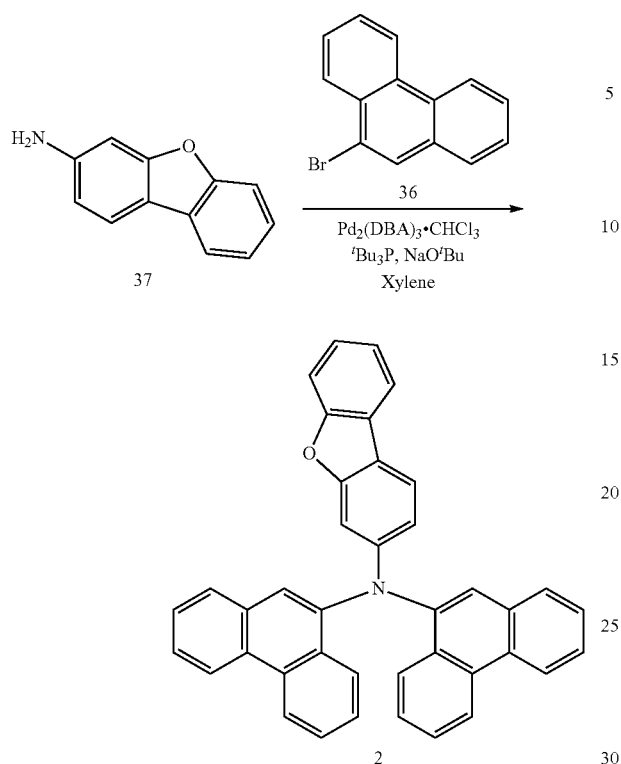

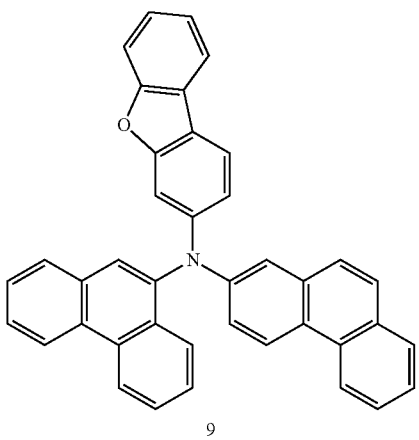

(Synthesis of Compound 2)

A mixture of Compound 37 (dibenzofuranamine, 2.32 g, 12.7 mmol), Compound 36 (bromophenanthrene, 6.68 g, 25.6 mmol), sodium-tert-butoxide (NaOtBu, 3.73 g, 38.0 mmol), tris(dibenzylideneacetone)palladium(0)chloroform adduct ($Pd_2(DBA)_3 \cdot CHCl_3$, 656 mg, 0.634 mmol), and anhydrous xylene (150 mL) was degassed, and an 1.6M-tri-tert-butylphosphine ($^tBu_3P$) solution (475 L, 0.760 mmol) was added thereto.

The mixture was heated and refluxed for about 12 hours, cooled, and filtered. The filtrate was concentrated and separated by directly using column chromatography to obtain Compound 2 (4.62 g, 68%) as a white powder.

(Identification Method of Compound 2)

The identification of Compound 2 was conducted by detecting molecular ion peak in FAB-MS measurement. The molecular weight of Compound 2 measured by FAB-MS was 535. In addition, the monoamine material for an organic EL device according to the present disclosure may be synthesized, for example, as follows.

(Synthesis of Compound 9)

A mixture of Compound 38 (diphenanthrylamine, 3.19 g, 8.64 mmol), Compound 39 (bromodibenzofuran, 2.35 g, 9.51 mmol), sodium-tert-butoxide (NaO$^t$Bu, 4.98 g, 51.9 mmol), tris(dibenzylideneacetone)dipalladium(0)chloroform adduct ($Pd_2(DBA)_3$-$CHCl_3$, 268 mg, 0.260 mmol), and anhydrous xylene (100 mL) was degassed, and an 1.6M-tri-tert-butylphosphine ($^tBu_3P$) solution (314 L, 0.520 mmol) was added thereto.

The mixture was heated and refluxed for about 10 hours, cooled, and filtered. The filtrate was concentrated and separated by directly using column chromatography to obtain Compound 9 (3.33 g, 72%) as a white powder. The identification of Compound 9 was conducted by detecting molecular ion peak in FAB-MS measurement. The molecular weight of Compound 9 measured by FAB-MS was 535.

(Synthesis of Compound 11)

Compound 11 was obtained by performing the same synthetic method of Compound 9 except for using 2-bromo-9,9-diphenylfluorene instead of Compound 39. In addition, the monoamine material for an organic EL device according to the present disclosure may be synthesized, for example, as follows.

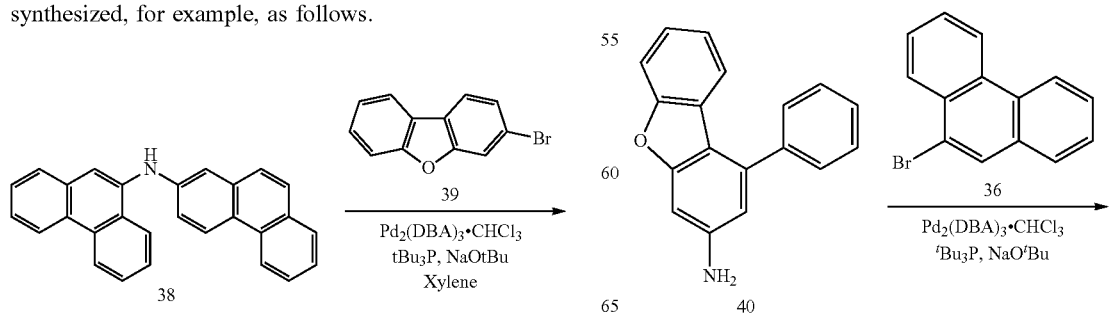

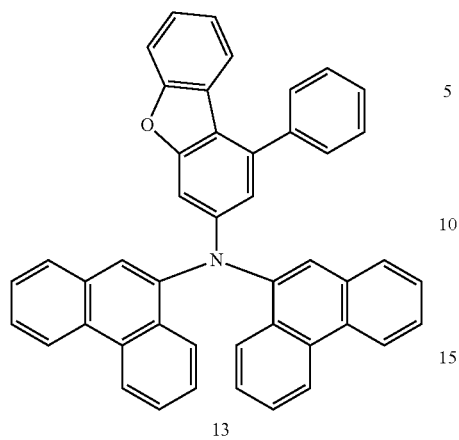

13

(Synthesis of Compound 13)

A mixture of Compound 40 (dibenzofuranamine, 2.30 g, 8.87 mmol), Compound 36 (bromophenanthrene, 4.78 g, 18.6 mmol), sodium-tert-butoxide (NaOtBu, 2.56 g, 2.66 mmol), tris(dibenzylideneacetone)dipalladium(0)chloroform adduct (Pd$_2$(DBA)$_3$·CHCl$_3$, 458 mg, 0.443 mmol), and anhydrous xylene (150 mL) was degassed, and an 1.6M-tri-tert-butylphosphine ($^t$Bu$_3$P) solution (554 L, 0.887 mmol) was added thereto. The mixture was heated and refluxed for about 18 hours, cooled, and filtered.

The filtrate was concentrated and separated by directly using column chromatography to obtain Compound 13 (3.20 g, 59%) as a white powder.

(Identification Method of Compound 13)

The identification of Compound 13 was conducted by detecting molecular ion peak in FAB-MS measurement. The molecular weight of Compound 13 measured by FAB-MS was 612.

In addition, the following Comparative Compound c1 to Comparative Compound c3 were prepared for comparison.

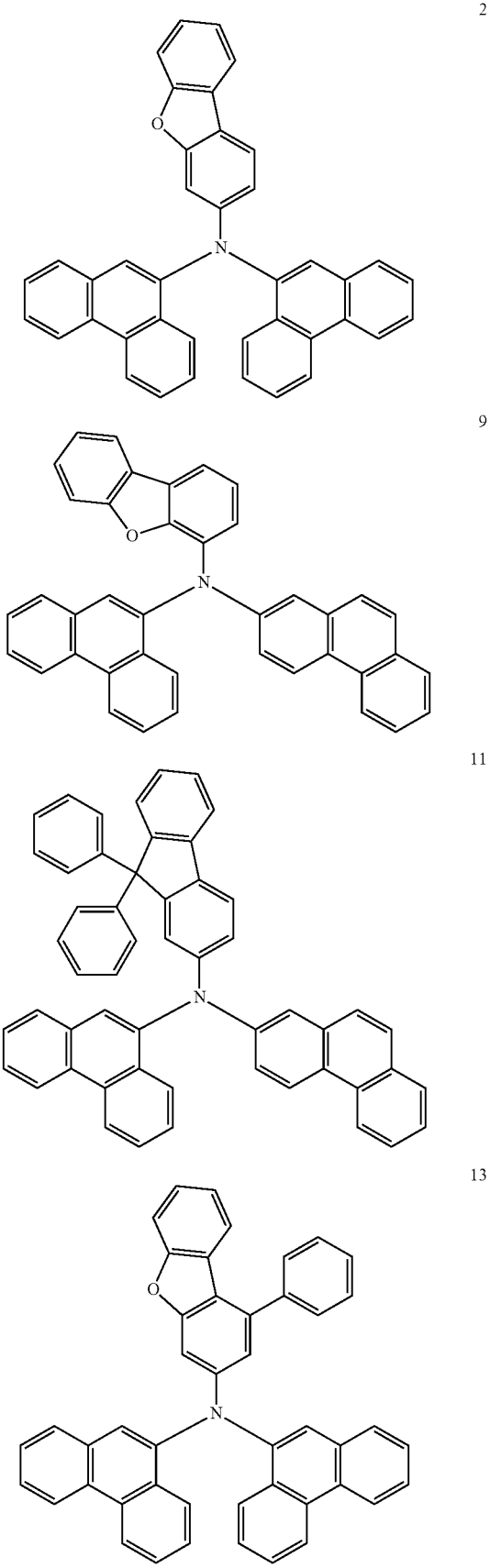

-continued

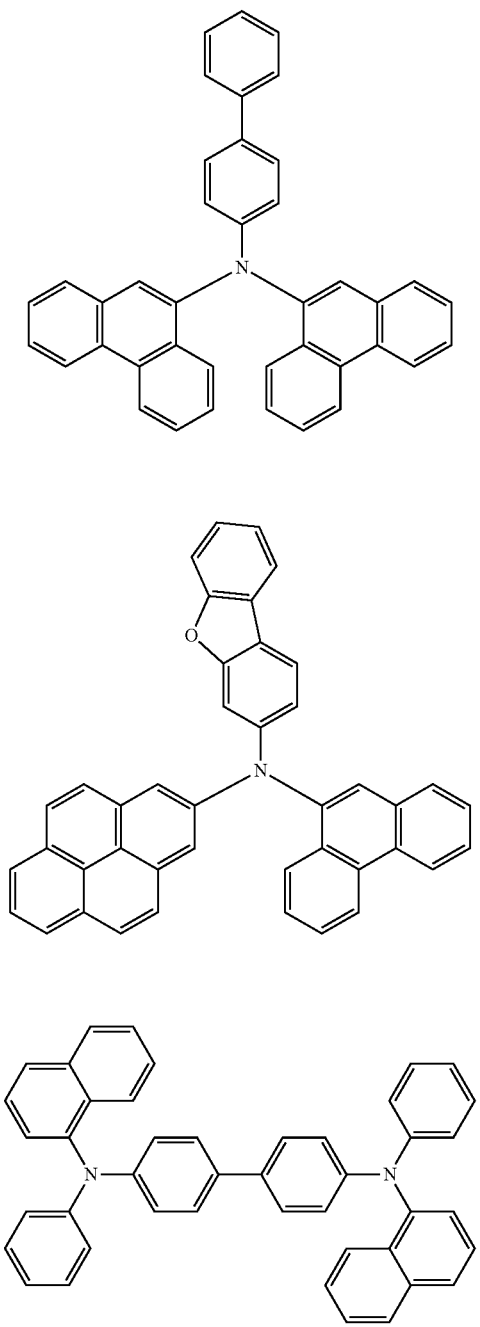

Organic EL devices 200 were formed by a similar method for forming the organic EL device 100 and using Compound 2, Compound 9, Compound 11, or Comparative Compound c1 to Comparative Compound c3, as hole transport materials.

In an embodiment, a substrate 202 was formed using a transparent glass substrate, an anode 204 was formed using ITO to a layer thickness of about 150 nm, a hole injection layer 206 was formed using 2-TNATA to a layer thickness of about 60 nm, a hole transport layer 208 was formed to a layer thickness of about 30 nm, an emission layer 210 was formed by doping ADN with 3% TBP to a layer thickness of about 25 nm, an electron transport layer 212 was formed using Alq$_3$ to a layer thickness of about 25 nm, an electron injection layer 214 was formed using LiF to a layer thickness of about 1 nm, and a cathode 216 was formed using Al to a layer thickness of about 100 nm.

With respect to the organic EL devices 200 thus manufactured, a driving voltage, emission efficiency, and half life were evaluated. Here, current efficiency represents a value at 10 mA/cm$^2$, and half life means luminance decrease time to half from initial luminance of 1,000 cd/m$^2$. Evaluation results are shown in the following Table 1.

TABLE 1

| | HTL | Voltage (V) | Emission efficiency (cd/A) | Half life (h) |
|---|---|---|---|---|
| Example 1 | Compound 1 | 6.7 | 7.3 | 2,200 |
| Example 2 | Compound 2 | 6.6 | 7.2 | 2,200 |
| Example 3 | Compound 9 | 6.6 | 7.2 | 2,400 |
| Example 4 | Compound 11 | 6.7 | 7.1 | 2,250 |
| Example 5 | Compound 13 | 6.7 | 7.4 | 2,150 |
| Comparative Example 1 | Comparative Compound c1 | 7.1 | 6.6 | 1,100 |
| Comparative Example 2 | Comparative Compound c2 | 6.7 | 5.1 | 900 |
| Comparative Example 3 | Comparative Compound c3 | 8.1 | 5.3 | 1,200 |

As clearly shown in Table 1, when comparing Examples 1 to 5, which use the monoamine material for an organic EL device according to the present disclosure as a hole transport material with Comparative Example 3 which uses Comparative Compound c3, which is a common hole transport material, the decrease of a driving voltage, and the increase of emission efficiency and device life were recognized.

In addition, when comparing Examples 1 to 5 with Comparative Example 1, the decrease of a driving voltage, and the increase of emission efficiency and device life were recognized.

In addition, when comparing Example 2 and Comparative Example 2 in which phenanthrene combined with an amine is replaced with pyrene, the improvement of emission efficiency and device life were recognized.

In addition, when comparing Example 2 with Example 3, Example 3 using a compound in which one of two phenanthryl groups is combined with the nitrogen atom (N) of an amine at position 9, and the other one is combined with the nitrogen atom (N) at position 2, that is, Compound 9 in which two phenanthryl groups are asymmetrically combined with the nitrogen atom (N) of an amine, has increased life when compared with Example 2.

The monoamine material for an organic EL device according to the present disclosure has improved hole transport property and electron tolerance and may inhibit electron transfer by introducing two phenanthrene parts to the nitrogen atom of an amine.

Accordingly, as clearly shown from the results in Table 1, an organic EL device having high efficiency and long life may be attained by using a monoamine material for an organic EL device according to the present disclosure as a material for at least one layer present between an anode and an emission layer.

According to the present disclosure, a material for an organic EL device having high efficiency and long life, and an organic EL device using the same may be provided.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A monoamine material for an organic electroluminescence (EL) device, represented by the following General Formula (1), Compound 24 or Compound 26:

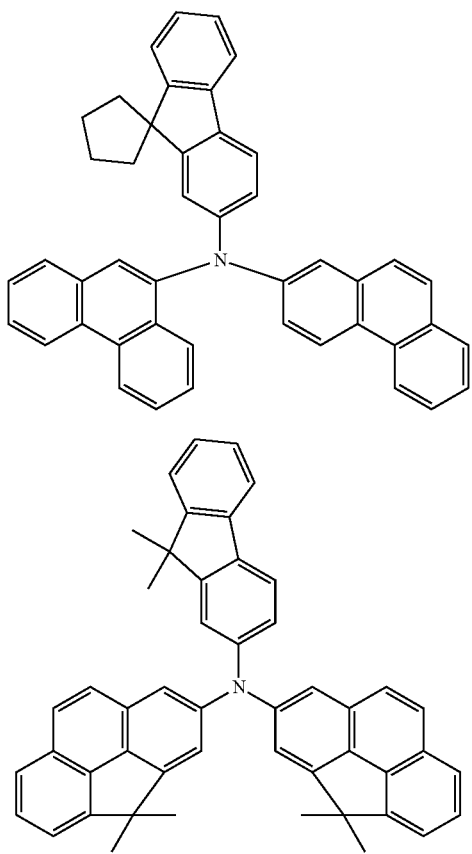

where $X^1$ is one selected from O, S, $CR^9R^{10}$, or N-$R^{11}$, $R^1$ to $R^{11}$ are each independently cyano group, alkyl having 10 or less carbon atoms, aryl having 6 to 30 carbon atoms for forming a ring, alkyloxy, alkylthio, trialkylsilyl, aryloxy, arylthio, triarylsilyl, alkyldiarylsilyl, dialkylarylsilyl, or heteroaryl having 2 to 30 carbon atoms for forming a ring, n is independently an integer of 0 to 4, m is an integer of 0 to 3, o is independently an integer of 0 to 2, and $R^1$ to $R^{11}$ can be combined with an adjacent group to form a saturated or unsaturated 5 to 7 member ring, and wherein when $X^1$ is $CR^9R^{10}$, n is 0.

2. The monoamine material for an organic EL device of claim 1, wherein a phenanthryl group in General Formula (1) is combined with a nitrogen atom at a position other than position 9 or position 10.

3. A monoamine material for an organic EL device, represented by the following General Formula (2):

[Formula 2]

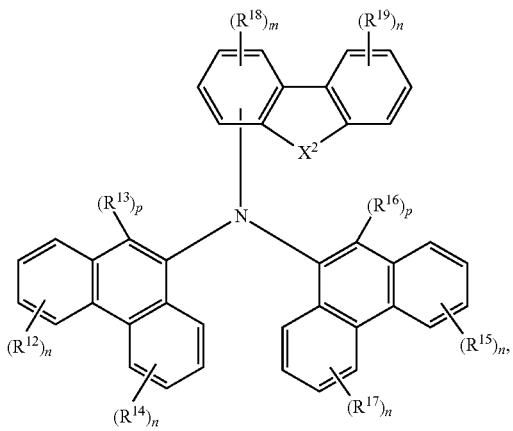

where $X^2$ is O or S, $R^{12}$ to $R^{19}$ are each independently cyano group, alkyl having 10 or less carbon atoms, aryl having 6 to 30 carbon atoms for forming a ring, alkyloxy, alkylthio, trialkylsilyl, aryloxy, arylthio, triarylsilyl, alkyldiarylsilyl, dialkylarylsilyl, or heteroaryl having 2 to 30 carbon atoms for forming a ring, n is independently an integer of 0 to 4, m is an integer of 0 to 3, p is independently an integer of 0 or 1, and $R^{12}$ to $R^{19}$ can be combined with an adjacent group to form a saturated or unsaturated 5 to 7 member ring.

4. An organic electroluminescence (EL) device comprising the monoamine material for an organic EL device described in claim 1 in at least one layer laminated between an emission layer and an anode.

5. An organic electroluminescence (EL) device comprising the monoamine material for an organic EL device described in claim 1 in a layer laminated between an emission layer and an anode, the layer being adjacent to the emission layer.

6. An organic electroluminescence (EL) device comprising a monoamine material for an organic EL device in at least one layer laminated between an emission layer and an anode wherein the monoamine material is a compound of the following compounds:

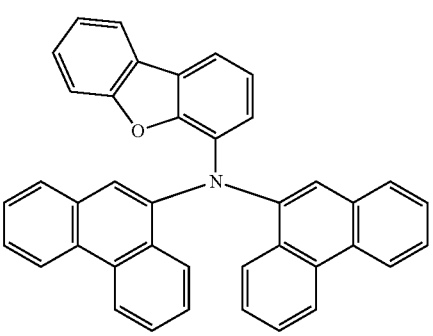

2
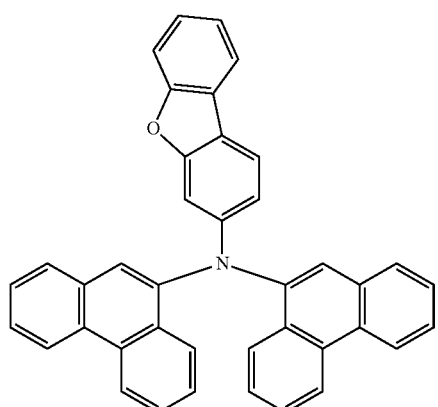
3
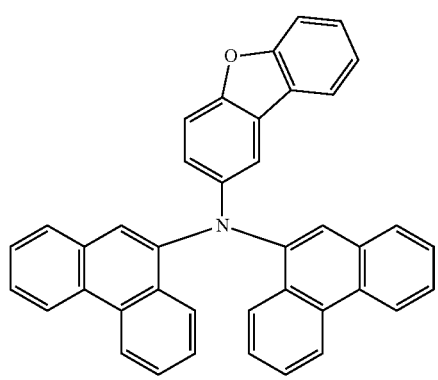
4
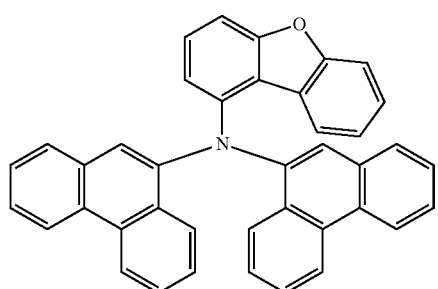
5
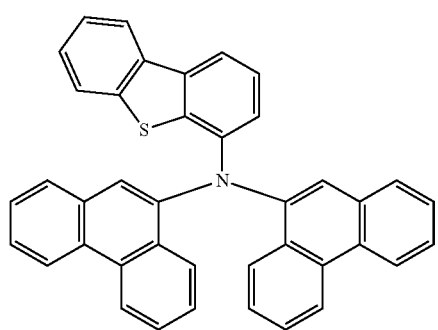
6
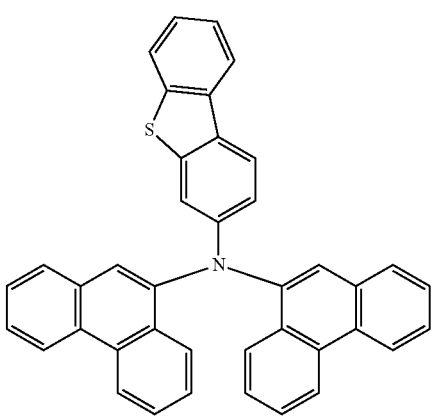
7
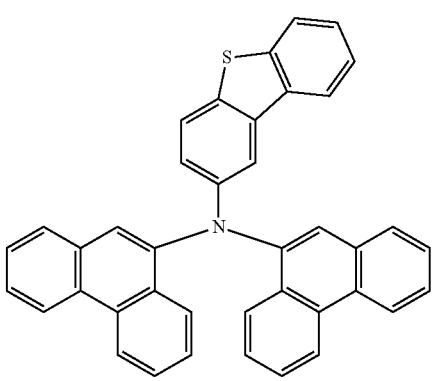
8
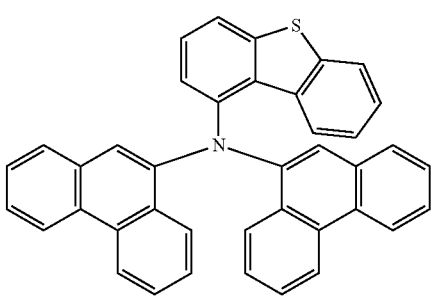
9
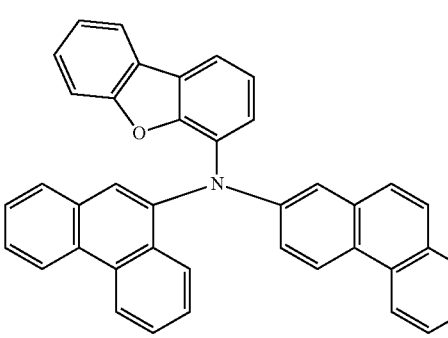

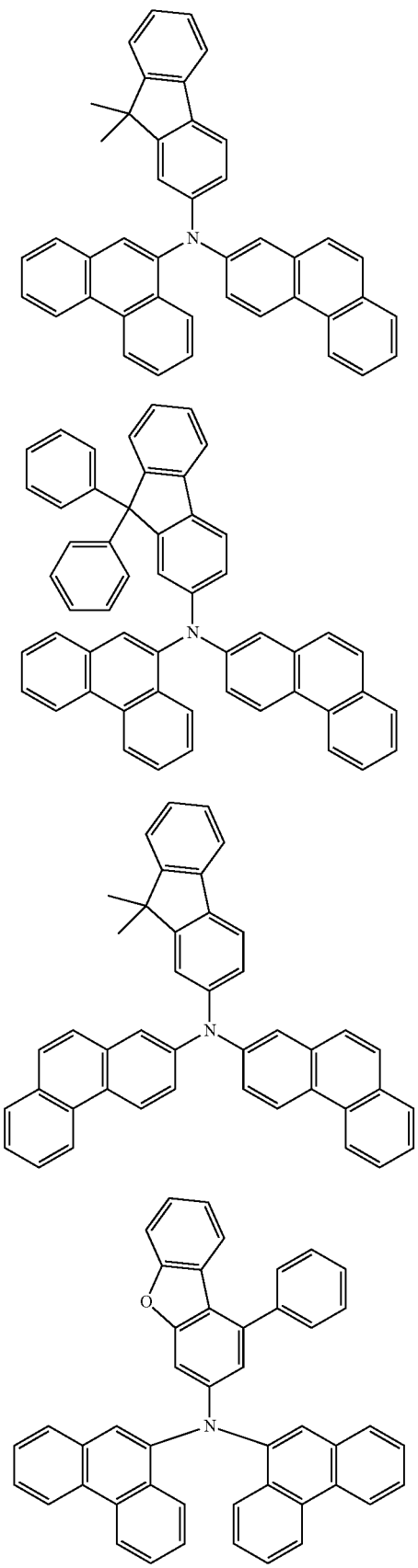
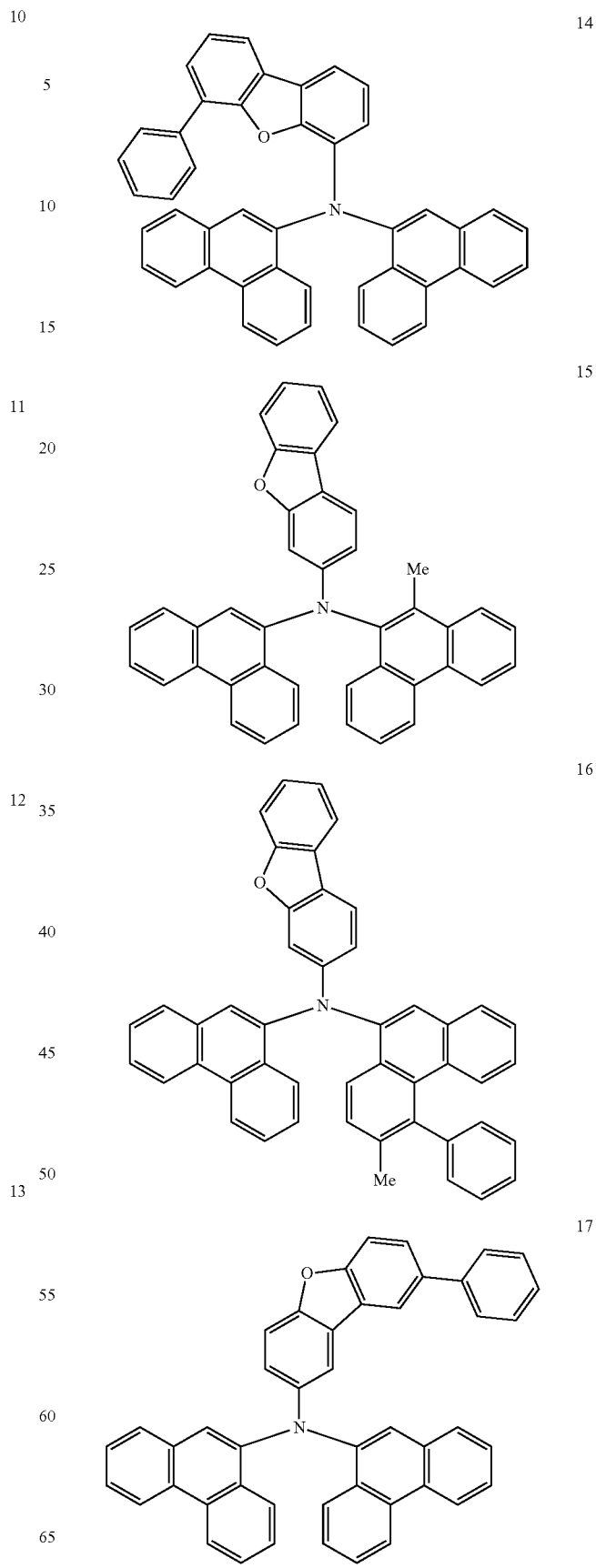

18
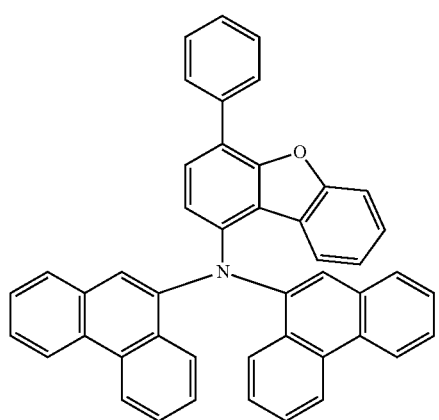
19
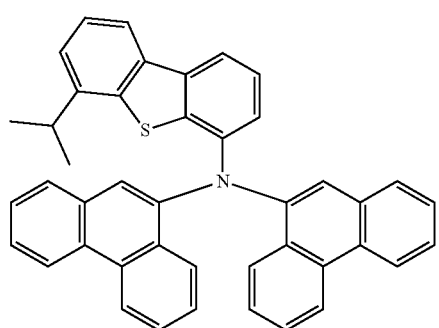
20
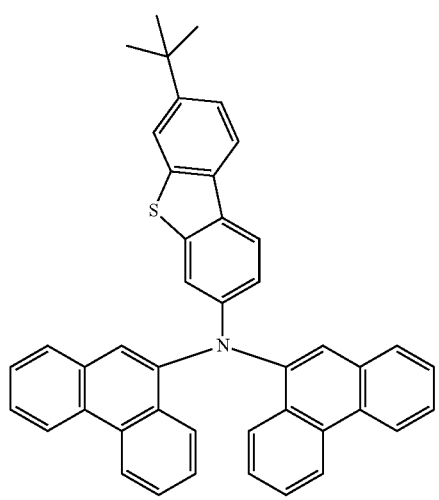
21
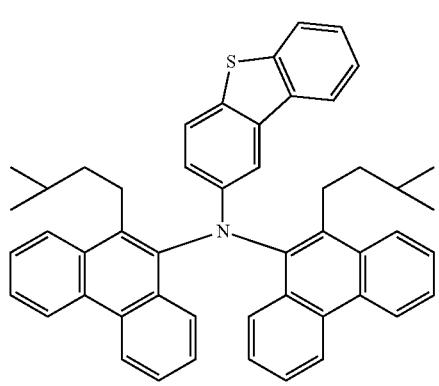
22
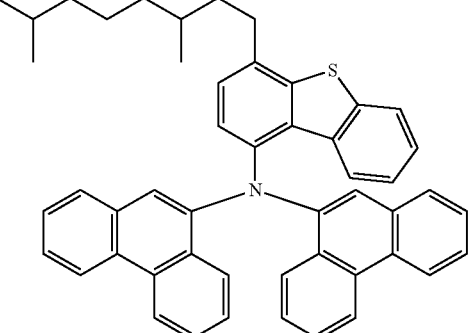
23
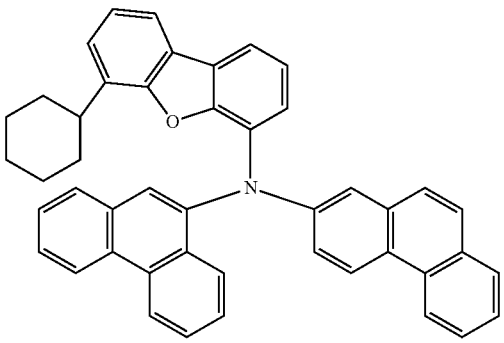
24
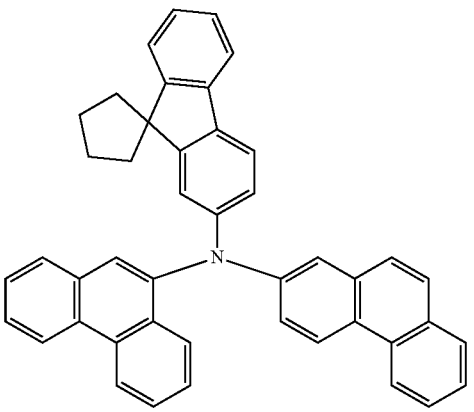
25
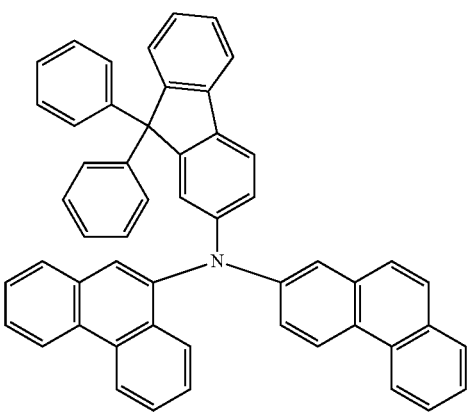

26
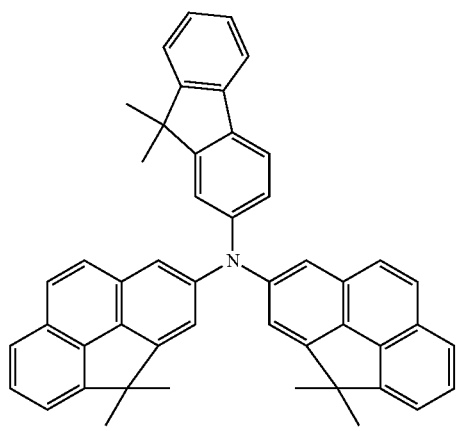
27
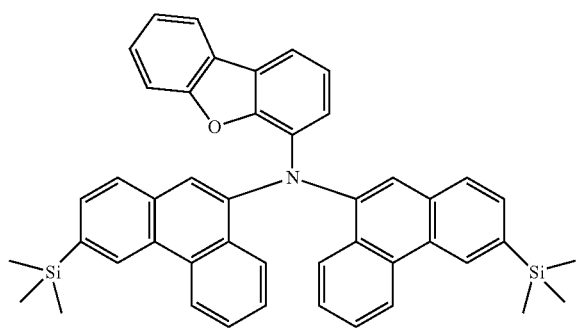
28
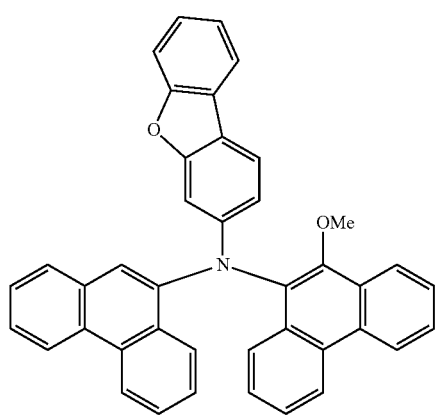
29
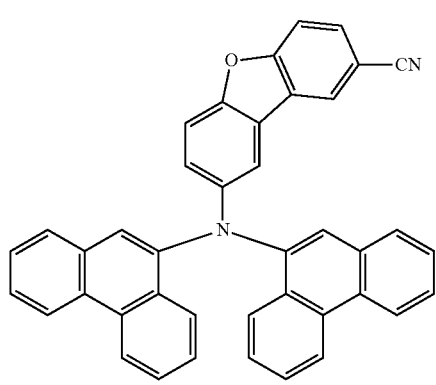
30
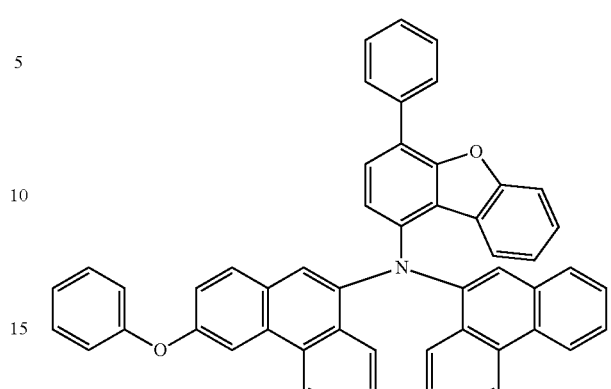
31
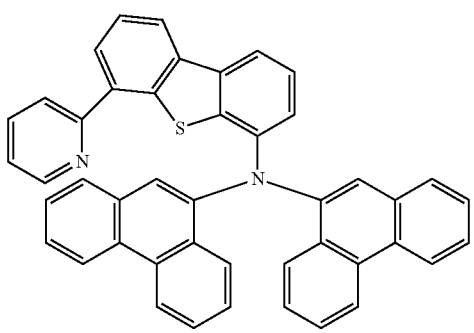
32
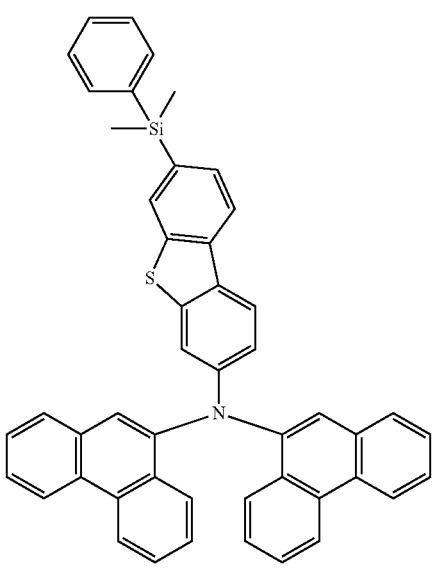

33

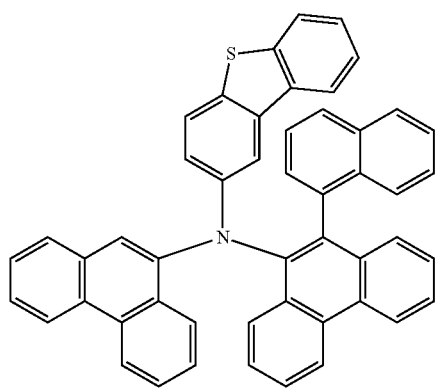

34

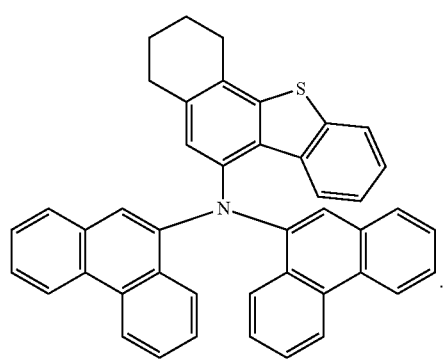

7. The organic electroluminescence (EL) device of claim 4, wherein the at least one layer comprises:
   a hole injection layer on the anode; and
   a hole transport layer between the anode and the hole injection layer; and
wherein the hole transport layer comprises the monoamine material for an organic EL device.

8. The organic electroluminescence (EL) device of claim 7, wherein the monoamine material for an organic EL device is a compound of the following compounds:

2

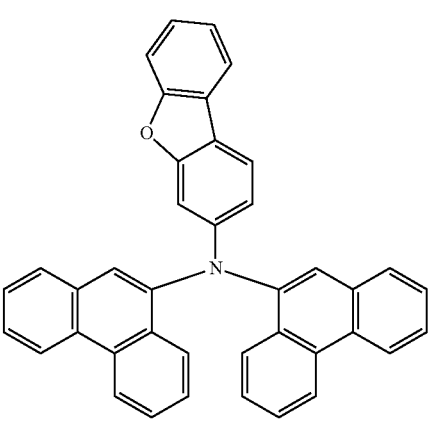

3

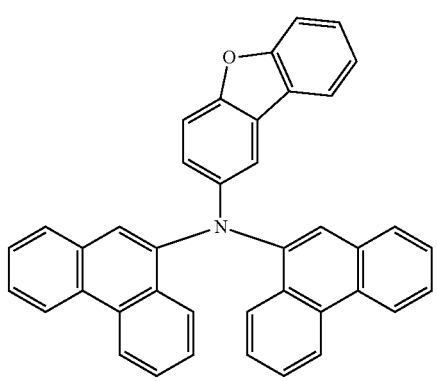

4

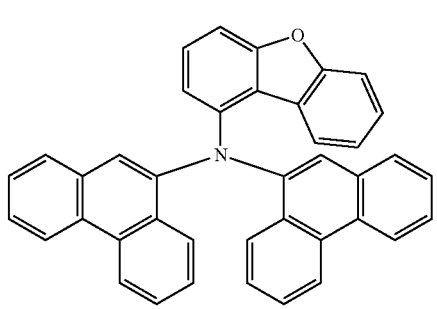

1

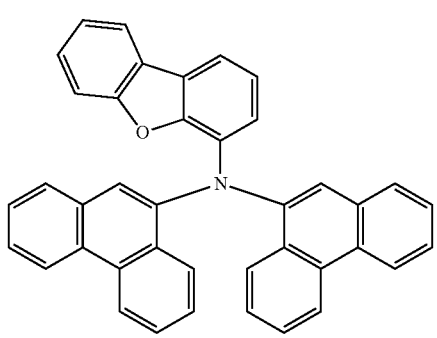

5

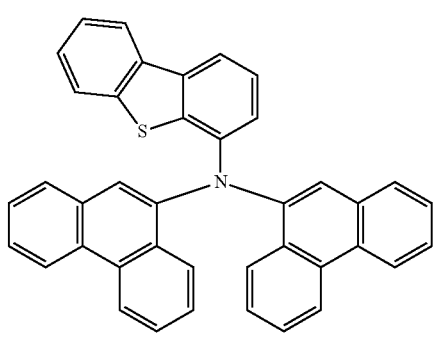

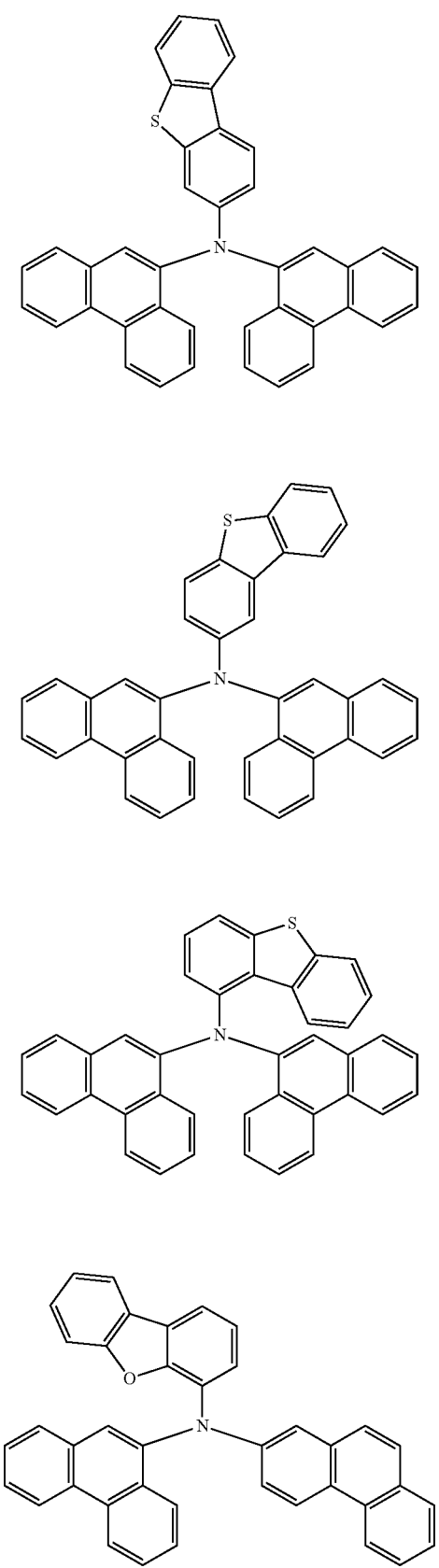
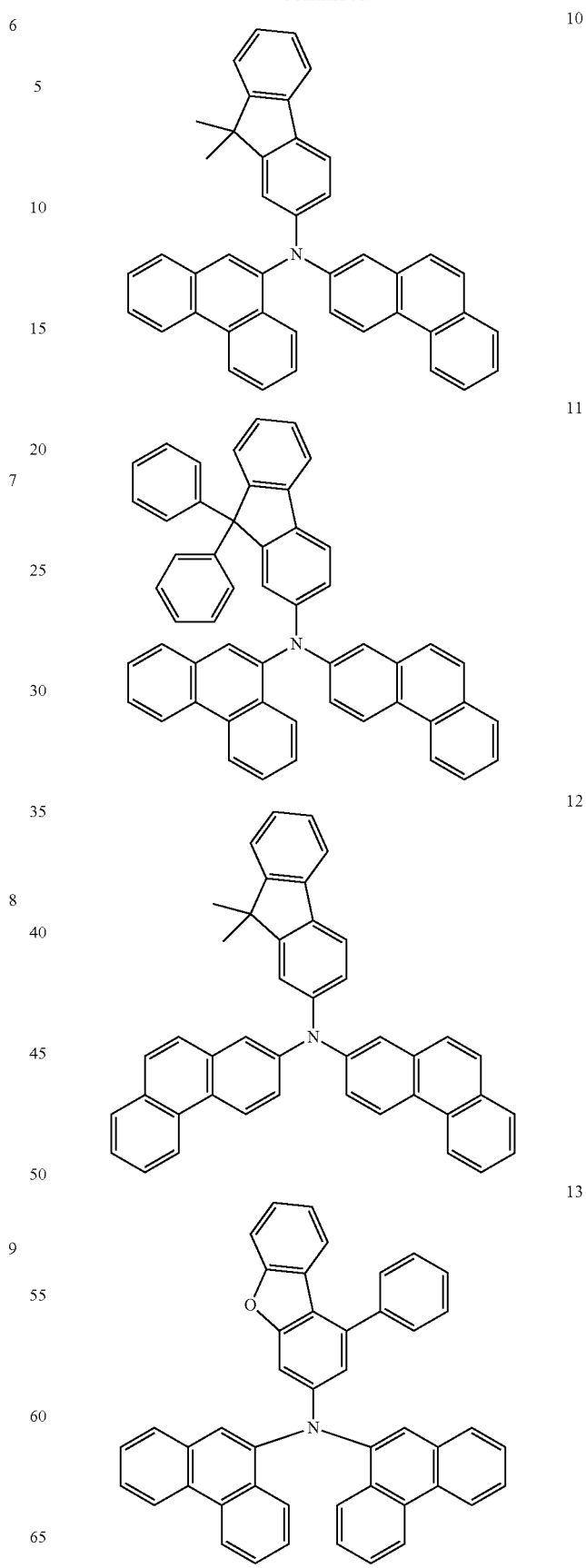

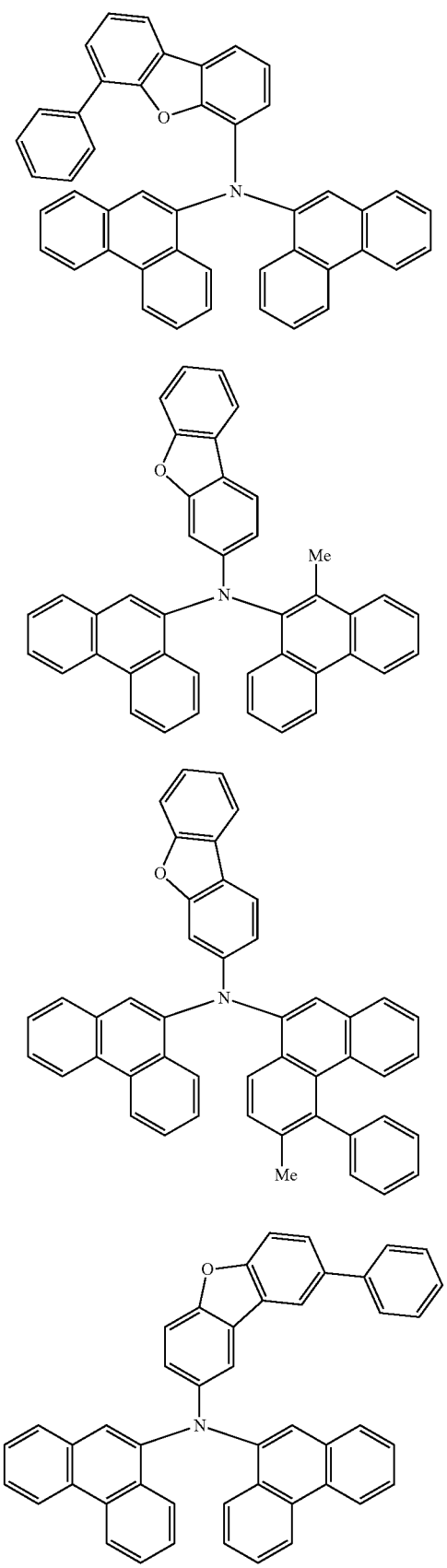
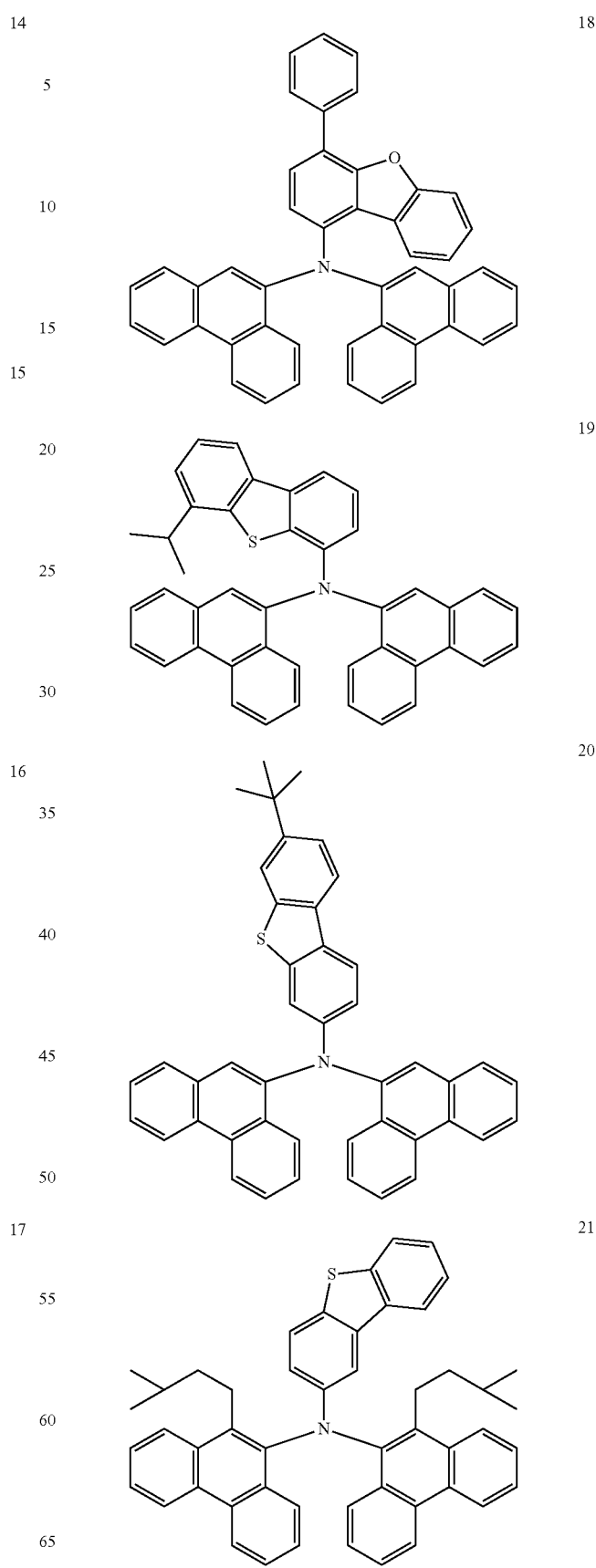

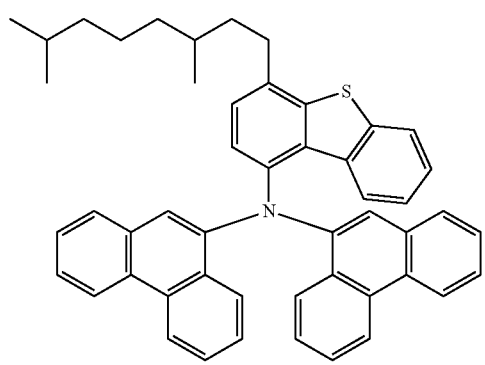
22
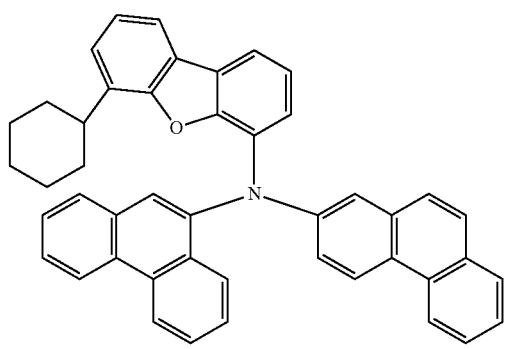
23
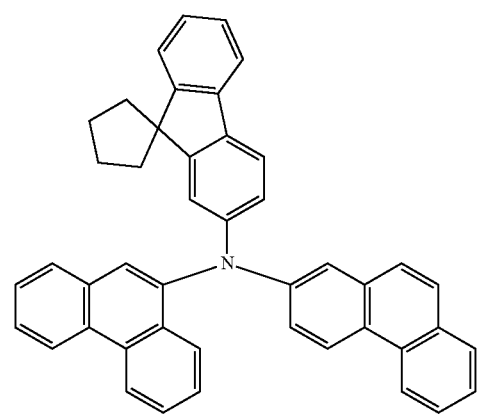
24
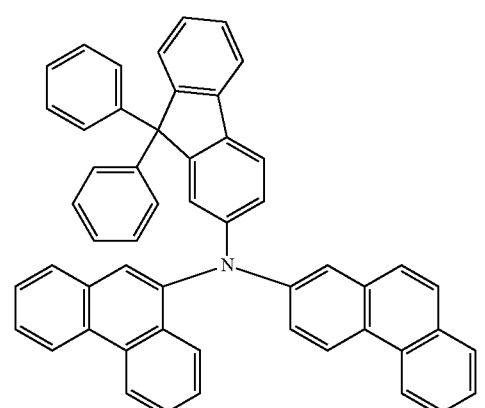
25
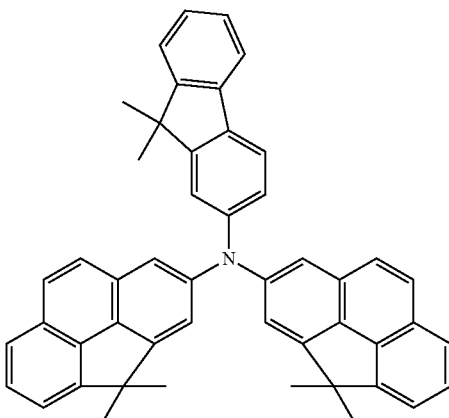
26
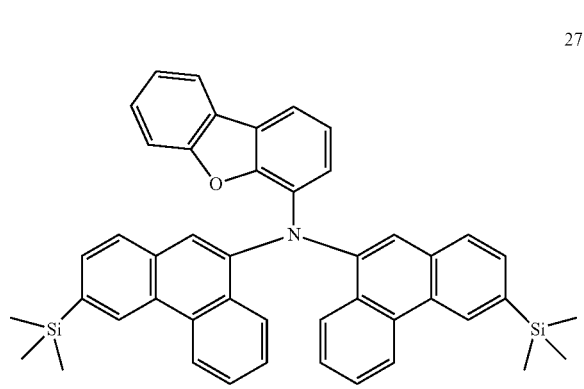
27
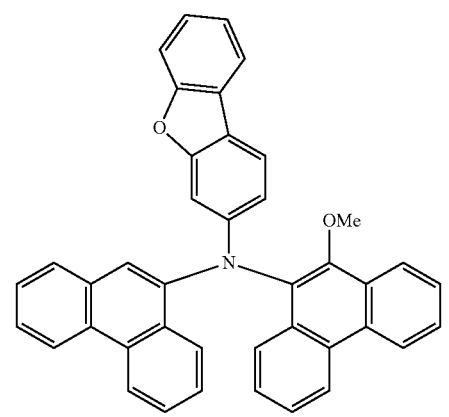
28
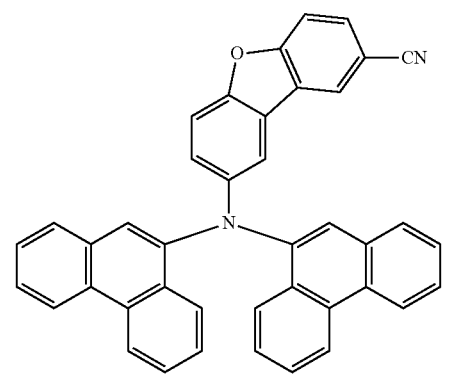
29

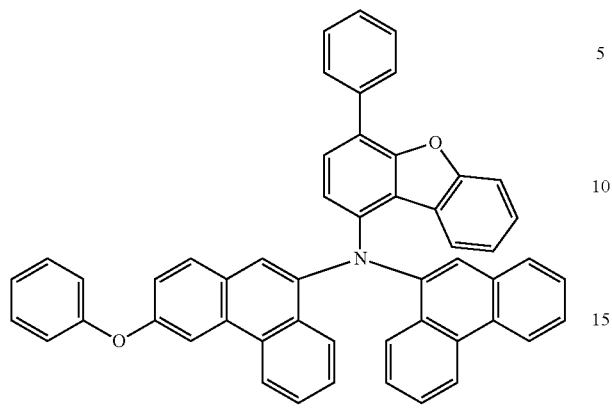
30
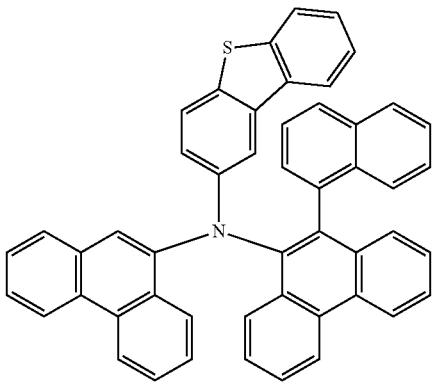
33
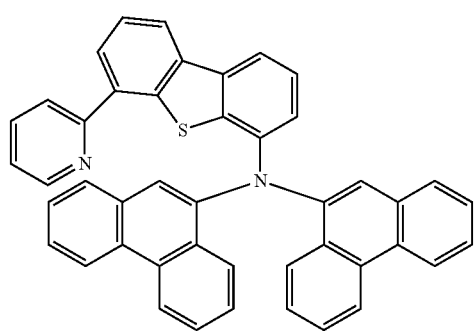
31
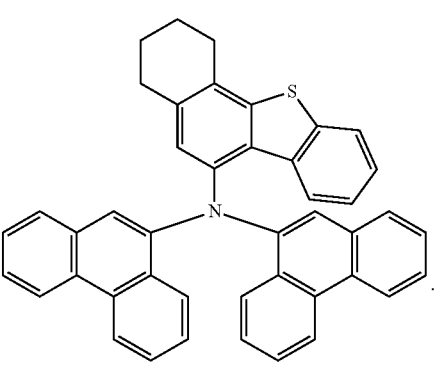
34
9. The monoamine material for an organic EL device of claim 1, wherein the monoamine material represented by General Formula (1) is a compound of the following compounds:
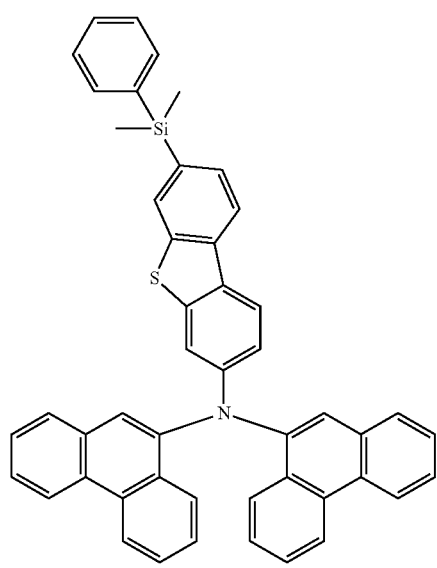
32
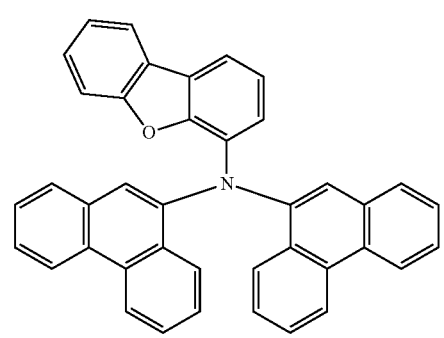
1

2
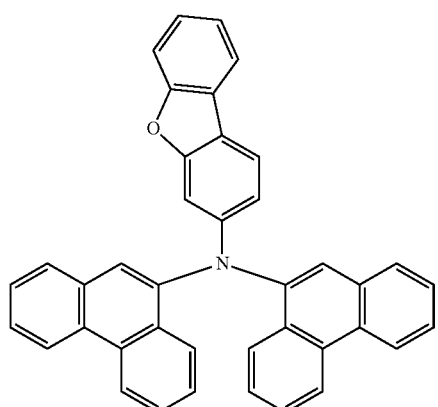
3
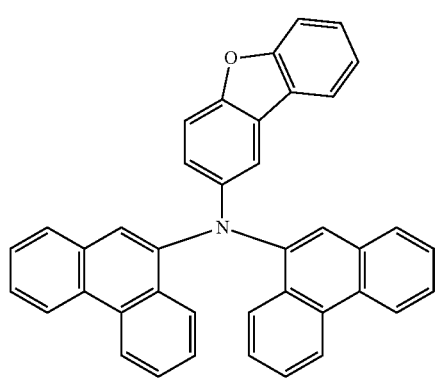
4
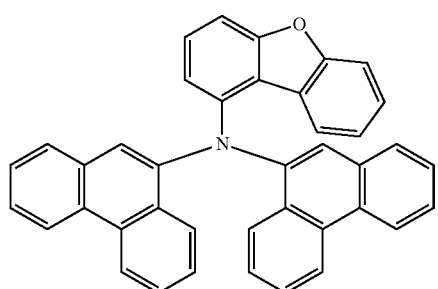
5
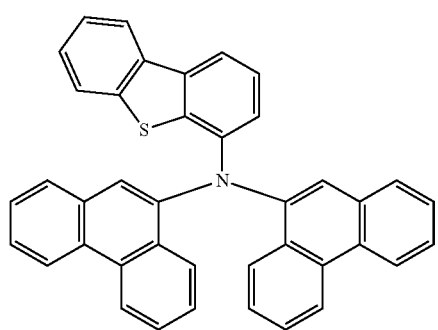
6
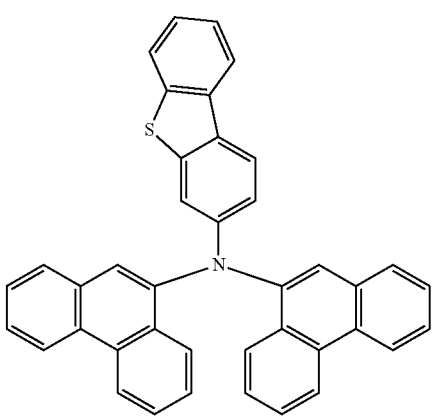
7
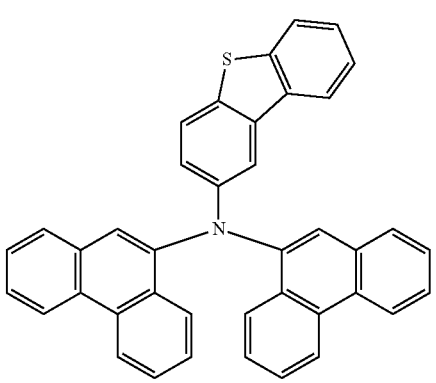
8
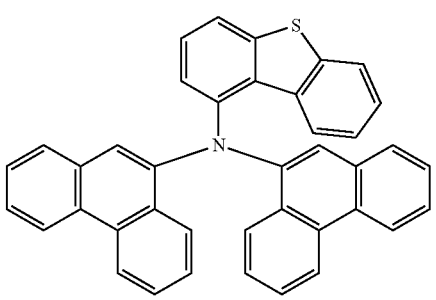
9
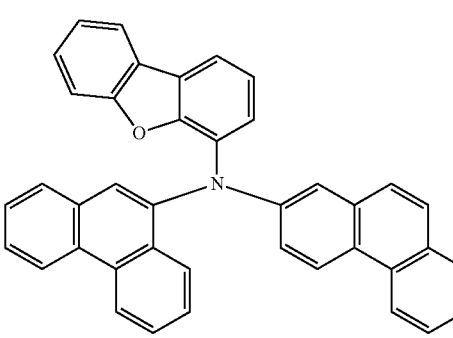

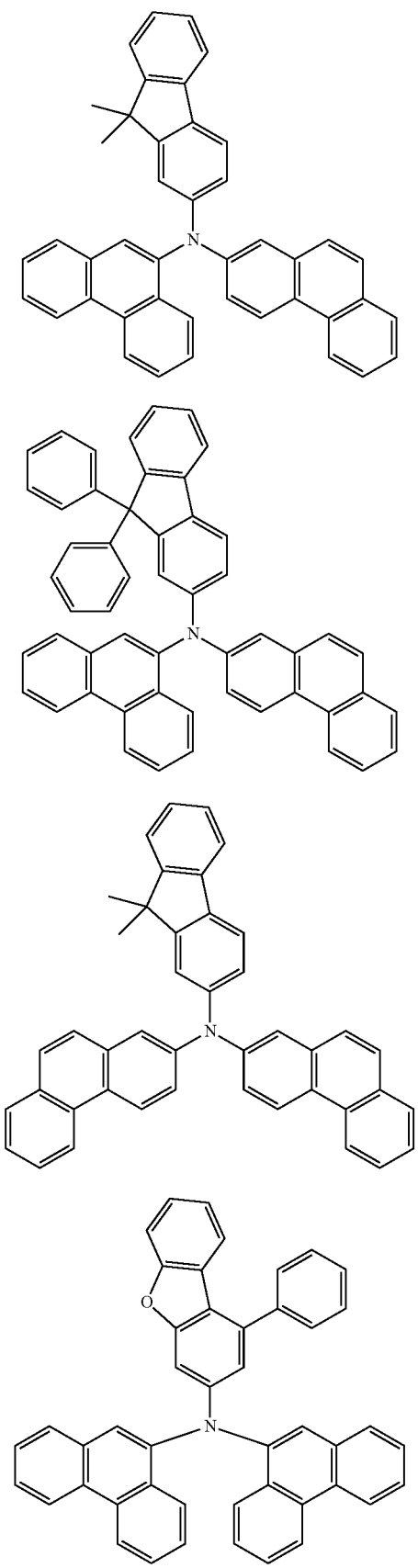
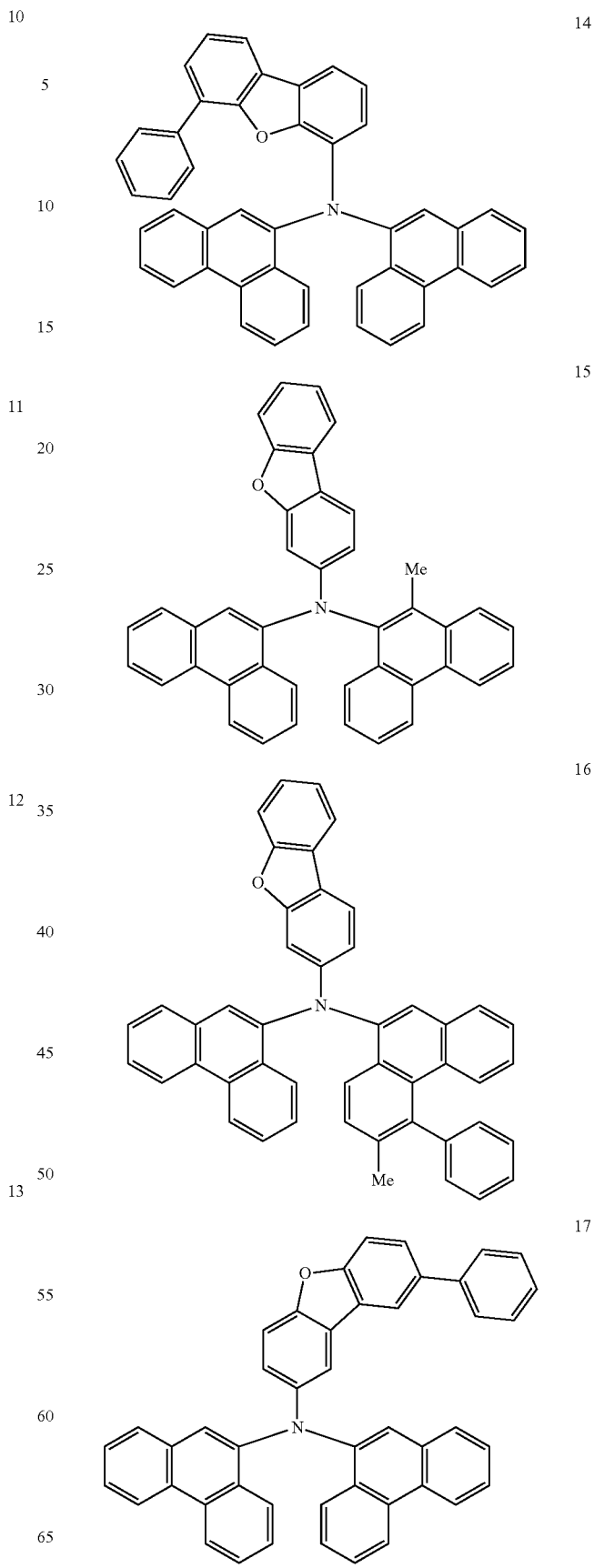

| 18 | 22 |
|---|---|
| 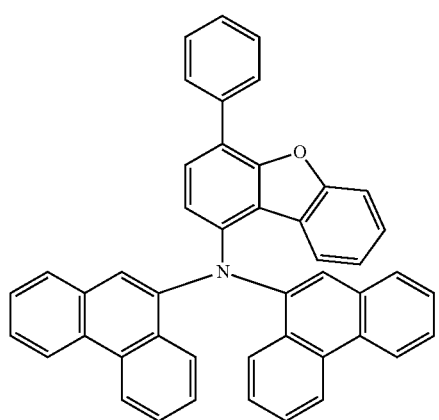 | 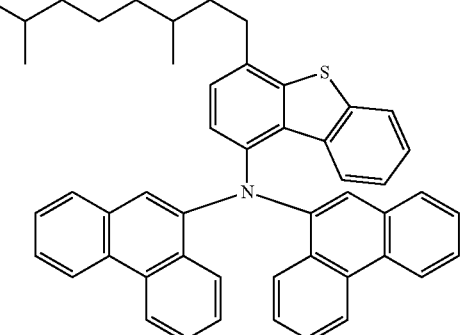 |
| 19 | 23 |
| 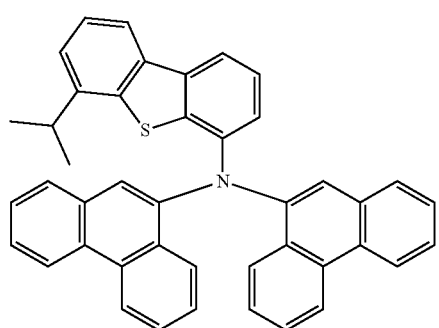 | 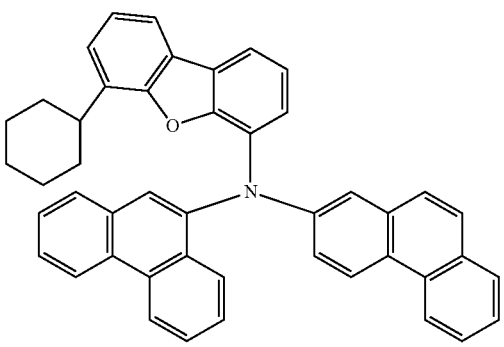 |
| 20 | 24 |
| 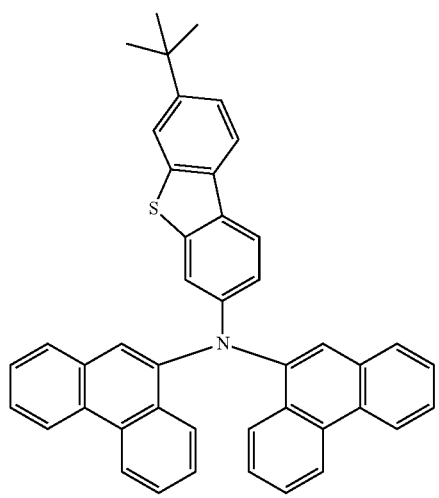 | 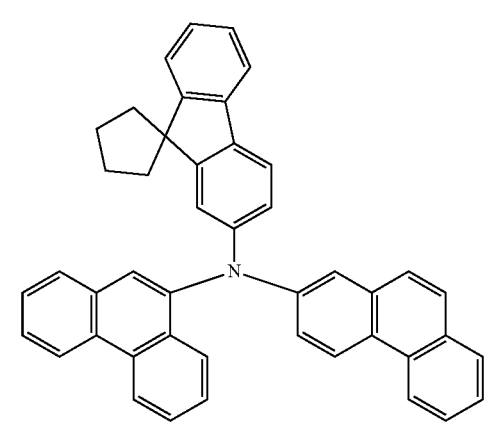 |
| 21 | 25 |
| 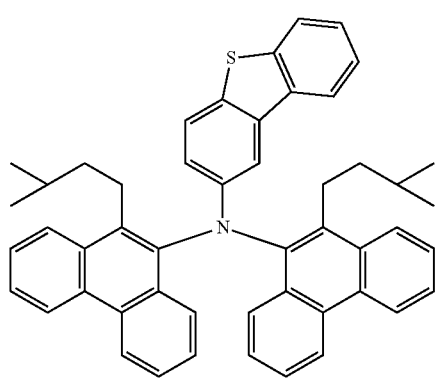 | 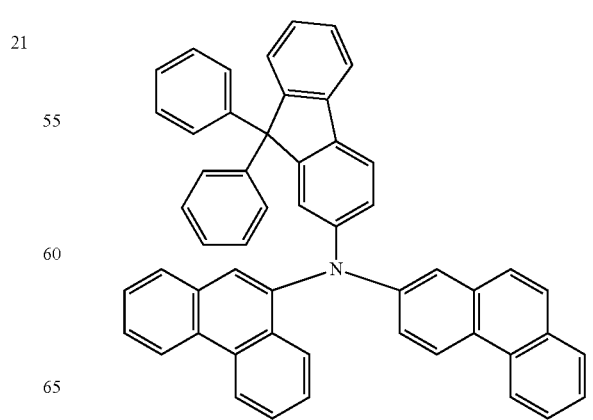 |

26
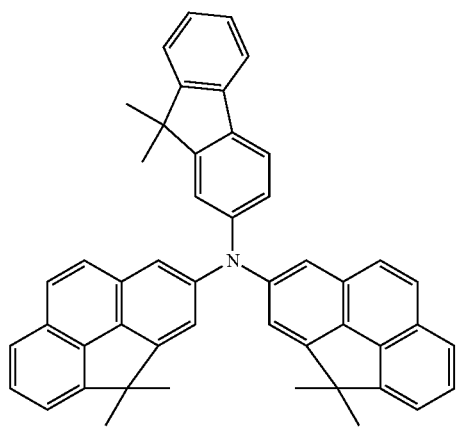
27
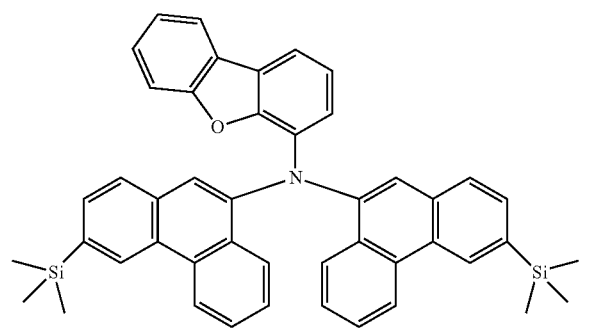
28
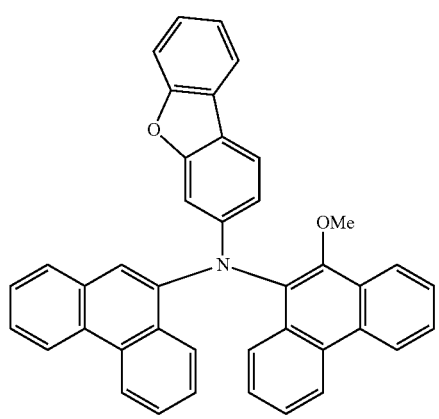
29
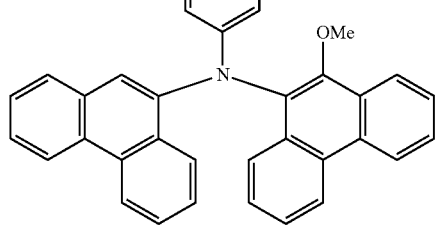
30
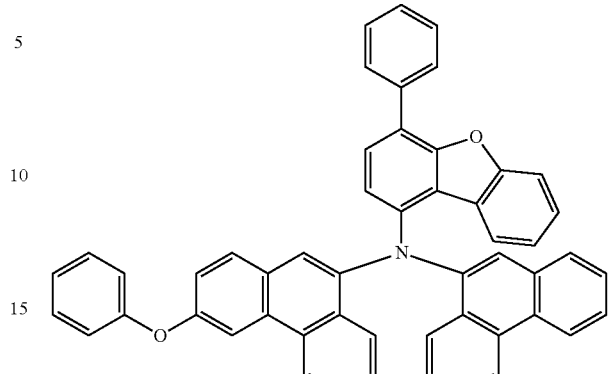
31
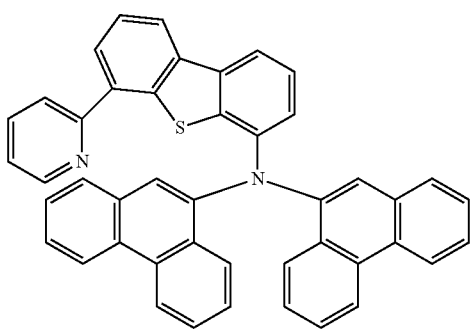
32
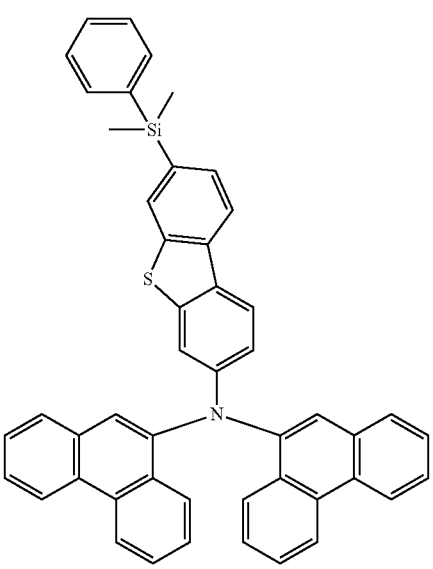

33
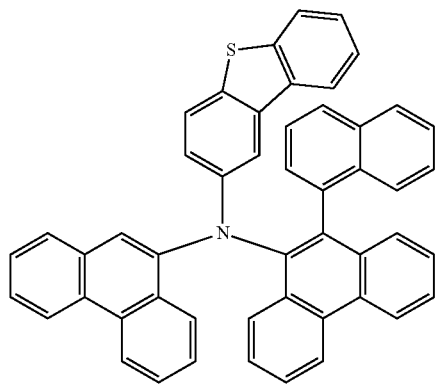
34
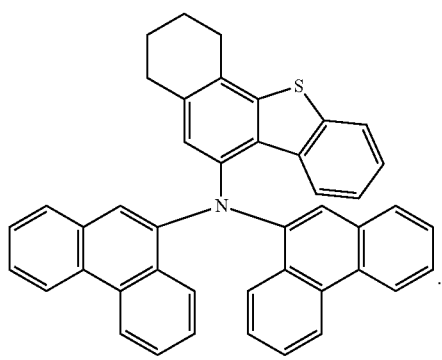
* * * * *